United States Patent
Cummins et al.

(10) Patent No.: US 8,590,760 B2
(45) Date of Patent: Nov. 26, 2013

(54) SURGICAL STAPLER

(75) Inventors: Christy Cummins, Naas (IE); James Coleman, Terenure (IE)

(73) Assignee: Abbott Vascular Inc., Redwood City, CA (US)

( * ) Notice: Subject to any disclaimer, the term of this patent is extended or adjusted under 35 U.S.C. 154(b) by 794 days.

(21) Appl. No.: 10/908,721

(22) Filed: May 24, 2005

(65) Prior Publication Data

US 2005/0274768 A1    Dec. 15, 2005

(30) Foreign Application Priority Data

May 25, 2004    (IE) .................................. S2004/0368

(51) Int. Cl.
*A61B 17/04* (2006.01)
(52) U.S. Cl.
USPC .... 227/175.1; 606/139; 606/142; 604/168.01
(58) Field of Classification Search
USPC ......... 606/219, 139, 75, 142–143; 227/175.1; 441/457; 604/168.01
See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 556,082 A | 3/1896 | Boeddinghaus |
| 1,088,393 A | 2/1914 | Backus |
| 1,242,139 A | 10/1917 | Callahan |
| 1,331,401 A | 2/1920 | Summers |
| 1,426,111 A | 8/1922 | Sacker |
| 1,480,935 A | 1/1924 | Gleason |
| 1,516,990 A | 11/1924 | Silverman |
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,108,206 A | 2/1938 | Meeker |
| 2,210,061 A | 8/1940 | Caminez |
| 2,254,620 A | 9/1941 | Miller |
| 2,316,297 A | 4/1943 | Southerland et al. |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

XP-002199926, Sep. 8, 2000, Anthony et al., Abstract Only.

(Continued)

*Primary Examiner* — Gary Jackson
*Assistant Examiner* — Diane Yabut
(74) *Attorney, Agent, or Firm* — Workman Nydegger; Randy Shen

(57) ABSTRACT

Methods and devices for closing a puncture wound in a liquid carrying vessel are provided. In one exemplary embodiment, a surgical stapler is provided having a locator tube with an inflatable member formed thereon and adapted to be positioned within a liquid carrying vessel adjacent a puncture wound, and a staple applying apparatus that is slidably disposed on a portion of the locator tube and that is adapted to apply a surgical staple to seal a puncture wound in a liquid carrying vessel.

39 Claims, 26 Drawing Sheets

(56) References Cited

U.S. PATENT DOCUMENTS

| | | |
|---|---|---|
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,682,180 A | 8/1972 | McFarlane |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,814,104 A | 6/1974 | Irnich et al. |
| 3,823,719 A | 7/1974 | Cummings |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,960,147 A | 6/1976 | Murray |
| 3,976,079 A | 8/1976 | Samuels et al. |
| 3,985,138 A | 10/1976 | Jarvik |
| 4,007,743 A | 2/1977 | Blake |
| 4,011,872 A | 3/1977 | Komiya |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,595,559 A | 6/1986 | Planchamp |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae |
| 4,836,204 A | 6/1989 | Landymore |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A * | 6/1990 | Green .......................... 606/143 |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |

(56) References Cited

U.S. PATENT DOCUMENTS

| | | |
|---|---|---|
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,158,566 A | 10/1992 | Pianetti |
| 5,160,339 A | 11/1992 | Chen et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,176,648 A | 1/1993 | Holmes et al. |
| 5,176,682 A | 1/1993 | Chow |
| 5,176,691 A | 1/1993 | Pierce |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,203,787 A | 4/1993 | Noblitt et al. |
| 5,209,756 A | 5/1993 | Seedhom et al. |
| 5,217,024 A | 6/1993 | Dorsey et al. |
| 5,217,471 A | 6/1993 | Burkhart |
| 5,219,359 A | 6/1993 | McQuilkin et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,237,996 A | 8/1993 | Waldman |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,258,015 A | 11/1993 | Li et al. |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway |
| 5,304,204 A | 4/1994 | Bregen |
| 5,306,254 A | 4/1994 | Nash et al. |
| 5,306,280 A | 4/1994 | Bregen et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,328,472 A * | 7/1994 | Steinke et al. ........... 604/102.02 |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Velez et al. |
| 5,395,030 A | 3/1995 | Kuramoto et al. |
| 5,403,330 A | 4/1995 | Tuason |
| 5,403,331 A | 4/1995 | Chesterfield et al. |
| 5,404,621 A | 4/1995 | Heinke |
| 5,409,499 A | 4/1995 | Yi |
| 5,411,520 A | 5/1995 | Nash et al. |
| 5,413,571 A | 5/1995 | Katsaros |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,558 A | 10/1995 | Kolesa et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A * | 11/1995 | Rothfuss et al. ........... 227/177.1 |
| 5,471,982 A | 12/1995 | Edwards et al. |
| 5,474,557 A | 12/1995 | Mai |
| 5,474,569 A | 12/1995 | Zinreich et al. |
| 5,474,572 A | 12/1995 | Hayhurst |
| 5,476,505 A | 12/1995 | Limon |
| 5,478,352 A | 12/1995 | Fowler |
| 5,478,353 A | 12/1995 | Yoon et al. |

(56) References Cited

U.S. PATENT DOCUMENTS

| | | |
|---|---|---|
| 5,478,354 A | 12/1995 | Tovey et al. |
| 5,486,195 A | 1/1996 | Myers et al. |
| 5,492,119 A | 2/1996 | Abrams |
| 5,497,933 A | 3/1996 | DeFonzo et al. |
| 5,501,698 A | 3/1996 | Roth et al. |
| 5,507,744 A | 4/1996 | Tay et al. |
| 5,507,755 A | 4/1996 | Gresl et al. |
| 5,514,159 A | 5/1996 | Matula et al. |
| 5,521,184 A | 5/1996 | Zimmerman |
| 5,522,840 A | 6/1996 | Krajicek |
| 5,527,322 A | 6/1996 | Klein et al. |
| 5,536,251 A | 7/1996 | Evard et al. |
| 5,536,267 A | 7/1996 | Edwards |
| 5,540,712 A | 7/1996 | Kleshinski et al. |
| 5,540,716 A | 7/1996 | Hlavacek |
| 5,543,520 A | 8/1996 | Zimmerman |
| 5,544,802 A | 8/1996 | Crainich |
| 5,547,474 A | 8/1996 | Kloeckl et al. |
| 5,560,532 A | 10/1996 | DeFonzo et al. |
| 5,562,684 A | 10/1996 | Kammerer |
| 5,571,120 A | 11/1996 | Yoon |
| 5,573,540 A | 11/1996 | Yoon |
| 5,573,784 A | 11/1996 | Badylak et al. |
| 5,575,771 A * | 11/1996 | Walinsky .................. 604/96.01 |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez |
| 5,593,422 A | 1/1997 | Muijs Van de Moer et al. |
| 5,593,425 A | 1/1997 | Bonutti et al. |
| 5,601,602 A | 2/1997 | Fowler |
| 5,609,597 A | 3/1997 | Lehrer |
| 5,611,986 A | 3/1997 | Datta et al. |
| 5,613,974 A | 3/1997 | Andreas et al. |
| 5,613,975 A | 3/1997 | Christy |
| 5,618,291 A | 4/1997 | Thompson et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,614 A | 5/1997 | Hart |
| 5,630,824 A | 5/1997 | Hart |
| 5,634,936 A | 6/1997 | Linden et al. |
| 5,643,318 A | 7/1997 | Tsukernik et al. |
| 5,645,553 A | 7/1997 | Kolesa et al. |
| 5,645,565 A | 7/1997 | Rudd et al. |
| 5,645,566 A | 7/1997 | Brenneman et al. |
| 5,645,567 A | 7/1997 | Crainich |
| 5,647,372 A | 7/1997 | Tovey et al. |
| 5,649,959 A | 7/1997 | Hannam et al. |
| D383,539 S | 9/1997 | Croley |
| 5,669,917 A | 9/1997 | Sauer et al. |
| 5,669,935 A | 9/1997 | Rosenman et al. |
| 5,672,174 A | 9/1997 | Gough et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,351 A | 10/1997 | Jamiolkowski et al. |
| 5,683,405 A | 11/1997 | Yacoubian et al. |
| 5,690,674 A | 11/1997 | Diaz |
| 5,693,061 A | 12/1997 | Pierce et al. |
| 5,695,504 A | 12/1997 | Gifford |
| 5,695,505 A | 12/1997 | Yoon |
| 5,695,524 A | 12/1997 | Kelley et al. |
| 5,700,273 A | 12/1997 | Buelna et al. |
| 5,709,224 A | 1/1998 | Behl et al. |
| 5,709,708 A | 1/1998 | Thal |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,720,765 A | 2/1998 | Thal |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,728,143 A | 3/1998 | Gough et al. |
| 5,732,872 A | 3/1998 | Bolduc et al. |
| 5,735,736 A | 4/1998 | Volk |
| 5,735,873 A | 4/1998 | MacLean |
| 5,735,875 A | 4/1998 | Bonutti et al. |
| 5,735,877 A | 4/1998 | Pagedas |
| 5,749,826 A | 5/1998 | Faulkner |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,759,189 A | 6/1998 | Ferragamo et al. |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,147 A | 7/1998 | Dolendo |
| 5,776,150 A | 7/1998 | Nolan et al. |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,845,657 A | 12/1998 | Carberry et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,928,231 A | 7/1999 | Klein et al. |

(56) References Cited

U.S. PATENT DOCUMENTS

| | | |
|---|---|---|
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,976,159 A | 11/1999 | Bolduc et al. |
| 5,976,161 A | 11/1999 | Kirsch et al. |
| 5,980,517 A | 11/1999 | Gough et al. |
| 5,984,934 A | 11/1999 | Ashby et al. |
| 5,984,948 A | 11/1999 | Hasson |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A * | 2/2000 | Kontos ............... 606/219 |
| 6,024,747 A | 2/2000 | Kontos |
| 6,024,750 A | 2/2000 | Mastri |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,066,160 A | 5/2000 | Colvin et al. |
| 6,068,603 A | 5/2000 | Suzuki |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,095,155 A | 8/2000 | Criscuolo |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,126,677 A | 10/2000 | Ganaja et al. |
| 6,143,004 A | 11/2000 | Davis |
| 6,143,017 A | 11/2000 | Thal |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,174,324 B1 | 1/2001 | Egan et al. |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,561 B1 | 5/2001 | Frazier et al. |
| 6,231,592 B1 | 5/2001 | Bonutti et al. |
| 6,245,079 B1 | 6/2001 | Nobles et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,898 B1 | 10/2001 | Edwards et al. |
| 6,305,891 B1 | 10/2001 | Burlingame |
| 6,306,081 B1 | 10/2001 | Ishikawa et al. |
| 6,309,416 B1 | 10/2001 | Swanson et al. |
| 6,319,258 B1 | 11/2001 | McAllen, III et al. |
| 6,322,580 B1 * | 11/2001 | Kanner ............... 606/213 |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |

(56) References Cited

U.S. PATENT DOCUMENTS

| | | | |
|---|---|---|---|
| 6,450,391 | B1 | 9/2002 | Kayan et al. |
| 6,458,130 | B1 | 10/2002 | Frazier et al. |
| 6,461,364 | B1 | 10/2002 | Ginn et al. |
| 6,461,366 | B1 | 10/2002 | Seguin |
| 6,482,224 | B1 | 11/2002 | Michler et al. |
| 6,488,692 | B1 | 12/2002 | Spence et al. |
| 6,500,115 | B2 | 12/2002 | Krattiger et al. |
| 6,506,210 | B1 | 1/2003 | Kanner |
| 6,508,828 | B1 | 1/2003 | Akerfeldt et al. |
| 6,514,280 | B1 | 2/2003 | Gilson |
| 6,517,498 | B1 | 2/2003 | Burbank et al. |
| 6,517,555 | B1 | 2/2003 | Caro |
| 6,517,569 | B2 | 2/2003 | Mikus et al. |
| 6,527,737 | B2 | 3/2003 | Kaneshige |
| 6,533,762 | B2 | 3/2003 | Kanner et al. |
| 6,533,812 | B2 | 3/2003 | Swanson et al. |
| 6,537,288 | B2 | 3/2003 | Vargas et al. |
| 6,547,806 | B1 | 4/2003 | Ding |
| 6,551,319 | B2 | 4/2003 | Lieberman |
| 6,558,349 | B1 | 5/2003 | Kirkman |
| 6,569,159 | B1 | 5/2003 | Edwards et al. |
| 6,569,173 | B1 | 5/2003 | Blatter et al. |
| 6,569,185 | B2 | 5/2003 | Ungs |
| 6,572,629 | B2 | 6/2003 | Kalloo et al. |
| 6,578,585 | B1 | 6/2003 | Stachowski et al. |
| 6,582,452 | B2 | 6/2003 | Coleman et al. |
| 6,582,482 | B2 | 6/2003 | Gillman et al. |
| 6,596,012 | B2 | 7/2003 | Akerfeldt et al. |
| 6,599,303 | B1 | 7/2003 | Peterson et al. |
| 6,599,311 | B1 | 7/2003 | Biggs et al. |
| 6,602,263 | B1 | 8/2003 | Swanson et al. |
| 6,610,072 | B1 | 8/2003 | Christy et al. |
| 6,613,059 | B2 | 9/2003 | Schaller et al. |
| 6,613,060 | B2 | 9/2003 | Adams et al. |
| 6,616,686 | B2 | 9/2003 | Coleman et al. |
| 6,620,165 | B2 | 9/2003 | Wellisz |
| 6,623,509 | B2 | 9/2003 | Ginn |
| 6,623,510 | B2 | 9/2003 | Carley et al. |
| 6,626,918 | B1 | 9/2003 | Ginn et al. |
| 6,626,919 | B1 | 9/2003 | Swanstrom |
| 6,626,920 | B2 | 9/2003 | Whayne |
| 6,632,197 | B2 | 10/2003 | Lyon |
| 6,632,238 | B2 | 10/2003 | Ginn et al. |
| 6,634,537 | B2 | 10/2003 | Chen |
| 6,645,205 | B2 | 11/2003 | Ginn |
| 6,645,225 | B1 | 11/2003 | Atkinson |
| 6,652,538 | B2 | 11/2003 | Kayan et al. |
| 6,652,556 | B1 | 11/2003 | VanTassel et al. |
| 6,663,633 | B1 | 12/2003 | Pierson, III |
| 6,663,655 | B2 | 12/2003 | Ginn et al. |
| 6,669,714 | B2 | 12/2003 | Coleman et al. |
| 6,673,083 | B1 | 1/2004 | Kayan et al. |
| 6,676,671 | B2 | 1/2004 | Robertson et al. |
| 6,676,685 | B2 | 1/2004 | Pedros et al. |
| 6,679,904 | B2 | 1/2004 | Gleeson et al. |
| 6,685,707 | B2 | 2/2004 | Roman et al. |
| 6,689,051 | B2 | 2/2004 | Nakada et al. |
| 6,689,147 | B1 | 2/2004 | Koster, Jr. |
| 6,695,867 | B2 | 2/2004 | Ginn et al. |
| 6,699,256 | B1 | 3/2004 | Logan et al. |
| 6,702,826 | B2 | 3/2004 | Liddicoat et al. |
| 6,712,836 | B1 | 3/2004 | Berg et al. |
| 6,712,837 | B2 | 3/2004 | Akerfeldt et al. |
| 6,719,777 | B2 | 4/2004 | Ginn et al. |
| 6,726,704 | B1 | 4/2004 | Loshakove et al. |
| 6,736,822 | B2 | 5/2004 | McClellan et al. |
| 6,743,195 | B2 | 6/2004 | Zucker |
| 6,743,243 | B1 | 6/2004 | Roy et al. |
| 6,743,259 | B2 | 6/2004 | Ginn |
| 6,745,079 | B2 | 6/2004 | King |
| 6,746,457 | B2 | 6/2004 | Dana et al. |
| 6,746,472 | B2 | 6/2004 | Frazier et al. |
| 6,749,621 | B2 | 6/2004 | Pantages et al. |
| 6,749,622 | B2 | 6/2004 | McGuckin et al. |
| 6,752,813 | B2 | 6/2004 | Goldfarb et al. |
| 6,755,842 | B2 | 6/2004 | Kanner et al. |
| 6,767,356 | B2 | 7/2004 | Kanner et al. |
| 6,776,785 | B1 | 8/2004 | Yencho et al. |
| 6,780,197 | B2 | 8/2004 | Roe et al. |
| 6,786,915 | B2 | 9/2004 | Akerfeldt et al. |
| 6,790,218 | B2 | 9/2004 | Jayaraman |
| 6,790,220 | B2 | 9/2004 | Morris et al. |
| 6,837,893 | B2 | 1/2005 | Miller |
| 6,837,906 | B2 | 1/2005 | Ginn |
| 6,846,319 | B2 | 1/2005 | Ginn et al. |
| 6,849,078 | B2 | 2/2005 | Durgin et al. |
| 6,860,895 | B1 | 3/2005 | Akerfeldt et al. |
| 6,890,343 | B2 | 5/2005 | Ginn et al. |
| 6,896,687 | B2 | 5/2005 | Dakov |
| 6,896,692 | B2 | 5/2005 | Ginn et al. |
| 6,904,647 | B2 | 6/2005 | Byers, Jr. |
| 6,913,607 | B2 | 7/2005 | Ainsworth et al. |
| 6,926,723 | B1 | 8/2005 | Mulhauser et al. |
| 6,926,731 | B2 | 8/2005 | Coleman et al. |
| 6,929,634 | B2 | 8/2005 | Dorros et al. |
| 6,942,641 | B2 | 9/2005 | Seddon |
| 6,942,674 | B2 | 9/2005 | Belef et al. |
| 6,969,397 | B2 | 11/2005 | Ginn |
| 6,984,238 | B2 | 1/2006 | Gifford, III et al. |
| 6,989,003 | B2 | 1/2006 | Wing et al. |
| 6,989,016 | B2 | 1/2006 | Tallarida et al. |
| 7,001,398 | B2 | 2/2006 | Carley et al. |
| 7,008,435 | B2 | 3/2006 | Cummins |
| 7,025,776 | B1 | 4/2006 | Houser et al. |
| 7,033,379 | B2 | 4/2006 | Peterson |
| 7,048,747 | B2 | 5/2006 | Arcia et al. |
| 7,060,084 | B1 | 6/2006 | Loshakove et al. |
| 7,063,661 | B2 | 6/2006 | Okada |
| 7,063,711 | B1 | 6/2006 | Loshakove et al. |
| 7,074,232 | B2 | 7/2006 | Kanner et al. |
| 7,076,305 | B2 | 7/2006 | Imran et al. |
| 7,083,635 | B2 | 8/2006 | Ginn |
| 7,087,064 | B1 | 8/2006 | Hyde |
| 7,108,709 | B2 | 9/2006 | Cummins |
| 7,108,710 | B2 | 9/2006 | Anderson |
| 7,111,768 | B2 | 9/2006 | Cummins et al. |
| 7,112,225 | B2 | 9/2006 | Ginn |
| 7,122,002 | B2 | 10/2006 | Okada |
| 7,144,411 | B2 | 12/2006 | Ginn et al. |
| 7,147,646 | B2 | 12/2006 | Dana et al. |
| 7,163,551 | B2 | 1/2007 | Anthony et al. |
| 7,169,158 | B2 | 1/2007 | Sniffin et al. |
| 7,169,164 | B2 | 1/2007 | Borillo et al. |
| 7,211,101 | B2 | 5/2007 | Carley et al. |
| 7,261,716 | B2 | 8/2007 | Strobel et al. |
| 7,270,672 | B1 | 9/2007 | Singer |
| 7,306,614 | B2 | 12/2007 | Weller et al. |
| 7,311,720 | B2 | 12/2007 | Mueller et al. |
| 7,316,704 | B2 | 1/2008 | Bagaoisan et al. |
| 7,316,706 | B2 | 1/2008 | Bloom et al. |
| 7,322,995 | B2 | 1/2008 | Bechman et al. |
| 7,326,230 | B2 | 2/2008 | Ravikumar |
| 7,331,979 | B2 | 2/2008 | Khosravi et al. |
| 7,335,220 | B2 | 2/2008 | Khosravi et al. |
| D566,272 | S | 4/2008 | Walburg et al. |
| 7,361,178 | B2 | 4/2008 | Hearn et al. |
| 7,361,183 | B2 | 4/2008 | Ginn |
| 7,361,185 | B2 | 4/2008 | O'Malley et al. |
| 7,393,363 | B2 | 7/2008 | Ginn |
| 7,396,359 | B1 | 7/2008 | Derowe et al. |
| 7,431,727 | B2 | 10/2008 | Cole et al. |
| 7,431,729 | B2 | 10/2008 | Chanduszko |
| 7,465,286 | B2 | 12/2008 | Patterson et al. |
| 7,507,200 | B2 | 3/2009 | Okada |
| 7,582,103 | B2 | 9/2009 | Young et al. |
| 7,582,104 | B2 | 9/2009 | Corcoran et al. |
| 7,597,706 | B2 | 10/2009 | Kanner et al. |
| 7,618,427 | B2 | 11/2009 | Ortiz et al. |
| 7,622,628 | B2 | 11/2009 | Bergin et al. |
| 7,645,285 | B2 | 1/2010 | Cosgrove et al. |
| 7,727,249 | B2 | 6/2010 | Rahmani |
| 7,731,655 | B2 | 6/2010 | Smith et al. |
| 7,749,249 | B2 | 7/2010 | Gelbart et al. |
| 7,780,696 | B2 | 8/2010 | Daniel et al. |

(56) References Cited

U.S. PATENT DOCUMENTS

| | | |
|---|---|---|
| 7,799,042 B2 | 9/2010 | Williamson, IV et al. |
| 7,819,895 B2 | 10/2010 | Ginn et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2001/0053909 A1 | 12/2001 | Nakada |
| 2002/0026208 A1 | 2/2002 | Roe et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0188275 A1 | 12/2002 | McGuckin |
| 2002/0188318 A1 | 12/2002 | Carley et al. |
| 2002/0193808 A1 | 12/2002 | Belef et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0267528 A1 | 12/2005 | Ginn et al. |
| 2005/0267530 A1 | 12/2005 | Cummins |
| 2005/0273136 A1 | 12/2005 | Belef et al. |
| 2005/0273137 A1 | 12/2005 | Ginn |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |

(56) References Cited

U.S. PATENT DOCUMENTS

| | | |
|---|---|---|
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0083230 A1 | 4/2007 | Javois |
| 2007/0083231 A1 | 4/2007 | Lee |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0287967 A1 | 11/2008 | Andreas et al. |
| 2008/0287988 A1 | 11/2008 | Smith et al. |
| 2008/0300628 A1 | 12/2008 | Ellingwood |
| 2008/0312686 A1 | 12/2008 | Ellingwood |
| 2008/0312740 A1 | 12/2008 | Wachter et al. |
| 2008/0319475 A1 | 12/2008 | Clark et al. |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0227938 A1 | 9/2009 | Fasching et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0114156 A1 | 5/2010 | Mehl |
| 2010/0114159 A1 | 5/2010 | Roorda et al. |
| 2010/0130965 A1 | 5/2010 | Sibbitt, Jr. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0178548 A1 | 7/2011 | Tenerz |
| 2011/0270282 A1 | 11/2011 | Lemke |
| 2012/0035630 A1 | 2/2012 | Roorda |
| 2012/0245603 A1 | 9/2012 | Voss |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |

FOREIGN PATENT DOCUMENTS

| | | |
|---|---|---|
| DE | 197 11 288 | 1/1998 |
| DE | 297 23 736 U1 | 4/1999 |
| DE | 19859952 | 2/2000 |
| DE | 102006056283 | 6/2008 |
| EP | 0 386 361 | 9/1990 |
| EP | 0534696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0664 | 2/2003 |
| IE | S 2002/0665 | 2/2003 |
| IE | S 2002/0451 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |

(56) References Cited

FOREIGN PATENT DOCUMENTS

| | | |
|---|---|---|
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO-00/56227 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/094748 | 11/2003 |
| WO | WO 03/071957 | 1/2004 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2008/031102 | 9/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 20010527 | 1/2001 |
| ZA | 200100528 | 1/2001 |

OTHER PUBLICATIONS

U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
2002/0072768, Office Action, Aug. 27, 2004.
2002/0072768, Office Action, Feb. 23, 2005.
2002/0072768, Office Action, Apr. 11, 2005.
2002/0072768, Office Action, Jul. 27, 2005.
2002/0072768, Office Action, Mar. 6, 2006.
2002/0072768, Office Action, May 24, 2006.
2002/0072768, Office Action, Oct. 26, 2006.
2002/0072768, Office Action, Apr. 19, 2007.
2002/0133193, Office Action, Nov. 4, 2004.
2002/0133193, Office Action, May 4, 2005.
2002/0133193, Office Action, Oct. 18, 2005.
2002/0133193, Notice of Allowance, Apr. 18, 2007.
2002/0133193, Notice of Allowance, Sep. 27, 2007.
2003/0078598, Office Action, Feb. 9, 2005.
2003/0078598, Office Action, May 26, 2005.
2003/0078598, Office Action, Oct. 4, 2005.
2003/0078598, Notice of Allowance, May 10, 2006.
2003/0078598, Notice of Allowance, Jul. 2, 2007.
2003/0195561, Office Action, Jun. 10, 2004.
2003/0195561, Notice of Allowance, Sep. 21, 2004.
2003/0195561, Office Action, Jan. 3, 2006.
2003/0195561, Issue Notification, Feb. 15, 2006.
2003/0195561, Office Action, May 16, 2006.
2003/0195561, Notice of Allowance, Dec. 28, 2006.
20030195561, Notice of Allowance, Jul. 10, 2007.
20030195561, Notice of Allowance, Aug. 2, 2007.
2004/0153123, Office Action, Sep. 22, 2006.
2004/0153123, Office Action, Jan. 31, 2007.
2004/0153123, Office Action, Sep. 18, 2007.
2004/0153122, Office Action, Nov. 30, 2005.
2004/0153122, Office Action, Aug. 23, 2006.
2004/0153122, Office Action, Feb. 13, 2007.
2004/0153122, Office Action, Sep. 12, 2007.
2004/0073255, Office Action, Sep. 15, 2006.
2004/0073255, Office Action, Apr. 18, 2007.
2004/0073236, Office Action, Sep. 19, 2006.
2004/0073236, Office Action, May 2, 2007.
2004/0009289, Office Action, Jun. 30, 2006.
2004/0009289, Office Action, Oct. 20, 2006.
2004/0009289, Office Action, May 29, 2007.
2004/0167570, Office Action, Oct. 30, 2006.
2004/0167570, Office Action, Apr. 17, 2007.
2004/0167570, Office Action, Aug. 31, 2007.
2005/0216057, Office Action, Feb. 6, 2007.
2005/0216057, Office Action, May 30, 2007.
2005/0234508, Office Action, Aug. 13, 2007.
2006/0135989, Office Action, Nov. 30, 2006.
2006/0135989, Office Action, Sep. 5, 2007.
2006/0195124, Office Action, Jun. 6, 2007.
2006/0195123, Office Action, May 14, 2007.
6,197,042, Notice of Allowance, Nov. 6, 2000.
6,197,042, Issue Notification, Feb. 15, 2001.
6,277,140, Office Action, Mar. 26, 2001.
6,277,140, Notice of Allowance, Jun. 4, 2001.
6,277,140, Issue Notification, Aug. 6, 2001.
6,391,048, Notice of Allowance, Mar. 26, 2001.
6,391,048, Office Action, Sep. 5, 2001.
6,391,048, Notice of Allowance, Feb. 11, 2002.
6,391,048, Issue Notification, May 3, 2002.
6,461,364, Notice of Allowance, May 6, 2002.
6,461,364, Issue Notification, Sep. 19, 2002.
6,582,452, Notice of Allowance, Jan. 31, 2003.
6,582,452, Issue Notification, Jun. 5, 2003.

(56) References Cited

OTHER PUBLICATIONS 6,616,686, Office Action, Dec. 17, 2002.
6,616,686, Notice of Allowance, Apr. 21, 2003.
6,616,686, Issue Notification, Aug. 21, 2003.
6,623,510, Notice of Allowance, Apr. 11, 2003.
6,623,510, Office Action, Jun. 9, 2003.
6,623,510, Issue Notification, Sep. 4, 2003.
6,632,238, Office Action, Feb. 26, 2003.
6,632,238, Notice of Allowance, Jun. 16, 2003.
6,632,238, Issue Notification, Sep. 25, 2003.
6,669,714, Office Action, Mar. 4, 2003.
6,669,714, Notice of Allowance, Jul. 28, 2003.
6,669,714, Issue Notification, Dec. 11, 2003.
6,695,867, Notice of Allowance, Sep. 29, 2003.
6,695,867, Issue Notification, Feb. 5, 2004.
6,719,777, Office Action, Feb. 20, 1987.
6,719,777, Notice of Allowance, Jul. 24, 1987.
6,719,777, Issue Notification, Mar. 25, 2004.
6,749,621, Notice of Allowance, Feb. 9, 2004.
6,749,621, Office Action, Apr. 13, 2004.
6,749,621, Issue Notification, May 27, 2004.
6,780,197, Office Action, Sep. 11, 2003.
6,780,197, Office Action, Feb. 9, 2004.
6,780,197, Notice of Allowance, Mar. 17, 2004.
6,780,197, Issue Notification, Aug. 5, 2004.
6,926,731, Office Action, Nov. 16, 2004.
6,926,731, Notice of Allowance, Apr. 6, 2005.
6,926,731, Issue Notification, Jul. 20, 2005.
6,942,674, Office Action, Sep. 29, 2004.
6,942,674, Notice of Allowance, May 13, 2005.
6,942,674, Issue Notification, Aug. 24, 2005.
7,001,398, Office Action, Mar. 22, 2005.
7,001,398, Notice of Allowance, Jul. 6, 2005.
7,001,398, Notice of Allowance, Oct. 5, 2005.
7,001,398, Issue Notification, Feb. 21, 2006.
7,008,435, Office Action, Apr. 20, 2005.
7,008,435, Office Action, Aug. 10, 2005.
7,008,435, Notice of Allowance, Oct. 18, 2005.
7,008,435, Issue Notification, Feb. 15, 2006.
7,108,709, Office Action, Jul. 27, 2004.
7,108,709, Office Action, Dec. 17, 2004.
7,108,709, Notice of Allowance, Mar. 9, 2005.
7,108,709, Office Action, Aug. 11, 2006.
7,108,709, Issue Notification, Aug. 30, 2006.
7,111,768, Office Action, Feb. 23, 2006.
7,111,768, Notice of Allowance, May 31, 2006.
7,111,768, Issue Notification, Sep. 6, 2006.
7,163,551, Office Action, Jan. 10, 2006.
7,163,551, Notice of Allowance, Sep. 20, 2006.
7,163,551, Issue Notification, Dec. 27, 2006.
7,211,101, Office Action, Aug. 10, 2005.
7,211,101, Office Action, Dec. 19, 2005.
7,211,101, Office Action, Apr. 21, 2006.
7,211,101, Notice of Allowance, Dec. 27, 2006.
7,211,101, Issue Notification, Apr. 11, 2007.
U.S. Appl. No. 10/541,083, Office Action, Oct. 16, 2007.
"Hand tool for forming telephone connections—comprises pliers with reciprocably driven ram crimping clip around conductors against anvil", Derwent-Acc-No. 1978-B8090A.
U.S. Appl. No. 10/356,214, Mar. 6, 2008, Office Action.
U.S. Appl. No. 10/435,104, Apr. 4, 2008, Notice of Allowance.
U.S. Appl. No. 10/787,073, Feb. 22, 2008, Office Action.
U.S. Appl. No. 11/113,549, Apr. 16, 2008, Office Action.
U.S. Appl. No. 10/682,459, Apr. 2, 2008, Office Action.
U.S. Appl. No. 10/786,444, Apr. 24, 2008, Office Action.
U.S. Appl. No. 10/638,115, Feb. 7, 2008, Office Action.
U.S. Appl. No. 10/264,306, May 26, 2005, Office Action.
U.S. Appl. No. 10/264,306, Feb. 4, 2008, Notice of Allowance.
U.S. Appl. No. 11/411,925, Feb. 5, 2008, Office Action.
U.S. Appl. No. 10/147,774, Feb. 4, 2008, Notice of Allowance.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

(56) References Cited

OTHER PUBLICATIONS

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 10/006,400, filed Apr. 2, 2008, Office Action.
U.S. Appl. No. 10/147,774, filed Jun. 30, 2008, Office Action.
U.S. Appl. No. 10/264,306, filed Jun. 27, 2008, Office Action.
U.S. Appl. No. 10/435,104, filed Sep. 26, 2008, Notice of Allowance.
U.S. Appl. No. 10/541,083, filed May 5, 2008, Office Action.
U.S. Appl. No. 10/541,083, filed Sep. 19, 2008, Notice of Allowance.
U.S. Appl. No. 10/616,832, filed Sep. 17, 2008, Office Action.
U.S. Appl. No. 10/667,144, filed May 12, 2008, Office Action.
U.S. Appl. No. 10/786,444, filed Oct. 17, 2008, Office Action.
U.S. Appl. No. 11/152,562, filed May 13, 2008, Office Action.
U.S. Appl. No. 11/198,811, filed Aug. 26, 2008, Office Action.
U.S. Appl. No. 11/344,891, filed Apr. 29, 2008, Office Action.
U.S. Appl. No. 11/406,203, filed May 23, 2008, Notice of Allowance.
U.S. Appl. No. 11/406,203, Sep. 22, 2008, Notice of Allowance.
U.S. Appl. No. 60/696,069, filed Jul. 1, 2005, Pantages et al.
U.S. Appl. No. 60/946,026, filed Jun. 25, 2007, Ellingwood.
McCarthy, et al., "Tension (Stay) Suture Bridge", J. of International College of Surgeons, 34(5), pp. 613-614 (Nov. 1960).
U.S. Appl. No. 10/006,400, Jan. 2, 2009, Office Action.
U.S. Appl. No. 10/264,306, Feb. 26, 2009, Office Action.
U.S. Appl. No. 10/305,923, Nov. 1, 2004, Office Action.
U.S. Appl. No. 10/305,923, Mar. 3, 2005, Notice of Allowance.
U.S. Appl. No. 10/356,214, Nov. 4, 2008, Office Action.
U.S. Appl. No. 10/435,104, Nov. 14, 2007, Notice of Allowance.
U.S. Appl. No. 10/435,104, Dec. 22, 2008, Notice of Allowance.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/541,083, Oct. 31, 2007, Office Action.
U.S. Appl. No. 10/541,083, Dec. 29, 2008, Notice of Allowance.
U.S. Appl. No. 10/638,115, Oct. 29, 2008, Office Action.
U.S. Appl. No. 10/682,459, Dec. 4, 2008, Office Action.
U.S. Appl. No. 10/787,073, Nov. 12, 2008, Office Action.
U.S. Appl. No. 11/152,562, Feb. 13, 2009, Office Action.
U.S. Appl. No. 11/344,793, Jan. 22, 2009, Office Action.
U.S. Appl. No. 11/344,891, Dec. 8, 2008, Office Action.
U.S. Appl. No. 11/344,891, Feb. 26, 2009, Office Action.
U.S. Appl. No. 11/396,731, Feb. 13, 2009, Office Action.
U.S. Appl. No. 11/411,925, Jan. 12, 2009, Office Action.
U.S. Appl. No. 11/427,297, Jan. 30, 2009, Office Action.
U.S. Appl. No. 11/461,323, May 2, 2007, Office Action.
U.S. Appl. No. 11/461,323, Oct. 29, 2007, Office Action.
U.S. Appl. No. 11/461,323, Apr. 25, 2008, Office Action.
U.S. Appl. No. 11/461,323, Nov. 6, 2008, Office Action.
U.S. Appl. No. 11/744,089, Nov. 26, 2008, Office Action.
20080210737, Jan. 23, 2009, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 12/393,877, filed Feb. 26, 2009, Ellingwood et al.
U.S. Appl. No. 12/403,277, filed Mar. 12, 2009, Coleman et al.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/680,837, Sep. 11, 2003, Issue Notification.
U.S. Appl. No. 10/006,400, Jul. 9, 2009, Notice of Allowance.
U.S. Appl. No. 10/147,774, Mar. 18, 2009, Office Action.
U.S. Appl. No. 10/264,306, Aug. 13, 2009, Office Action.
U.S. Appl. No. 10/356,214, Apr. 29, 2009, Office Action.
U.S. Appl. No. 10/517,004, Jun. 26, 2009, Notice of Allowance.
U.S. Appl. No. 10/541,083, Apr. 16, 2009, Notice of Allowance.
U.S. Appl. No. 10/616,832, Jul. 21, 2009, Office Action.
U.S. Appl. No. 10/638,115, May 7, 2009, Notice of Allowance.
U.S. Appl. No. 10/667,144, Mar. 24, 2009, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/669,313, Nov. 15, 2006, Issue Notification.
U.S. Appl. No. 10/682,459, Jun. 10, 2009, Office Action.
U.S. Appl. No. 10/786,444, Jun. 18, 2009, Office Action.
U.S. Appl. No. 10/787,073, Aug. 13, 2009, Office Action.
U.S. Appl. No. 11/048,503, Mar. 13, 2009, Office Action.
U.S. Appl. No. 11/048,503, Jun. 26, 2009, Office Action.
U.S. Appl. No. 11/113,549, Jul. 21, 2009, Office Action.
U.S. Appl. No. 11/152,562, Jul. 6, 2009, Office Action.
U.S. Appl. No. 11/198,811, Sep. 22, 2009, Office Action.
U.S. Appl. No. 11/344,868, Mar. 25, 2009, Office Action.
U.S. Appl. No. 11/390,586, Jun. 24, 2009, Office Action.
U.S. Appl. No. 11/396,141, May 22, 2009, Restriction Requirement.
U.S. Appl. No. 11/396,141, Aug. 26, 2009, Office Action.
U.S. Appl. No. 11/396,731, May 22, 2009, Office Action.
U.S. Appl. No. 11/406,203, Mar. 3, 2009, Office Action.
U.S. Appl. No. 11/406,203, Sep. 16, 2009, Office Action.
U.S. Appl. No. 11/411,925, Sep. 10, 2009, Office Action.
U.S. Appl. No. 11/427,297, Sep. 15, 2009, Office Action.
U.S. Appl. No. 11/461,323, Jul. 27, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/744,089, Aug. 14, 2009, Office Action.

(56) References Cited

OTHER PUBLICATIONS

U.S. Appl. No. 11/958,295, Aug. 27, 2009, Office Action.
U.S. Appl. No. 12/106,937, Mar. 30, 2009, Office Action.
U.S. Appl. No. 29/296,370, Apr. 1, 2009, Notice of Allowance.
U.S. Appl. No. 10/638,115, Dec. 22, 2010, Issue Notification.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 11/113,549, Jan. 4, 2011, Office Action.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 12/897,358, filed Jan. 12, 2012, Notice of Allowance.
U.S. Appl. No. 12/608,773, Jan. 7, 2013, Office Action.
U.S. Appl. No. 13/490,143, Jan. 4, 2013, Restriction Requirement.
U.S. Appl. No. 13/615,547, Jan. 18, 2013, Office Action.
U.S. Appl. No. 10/435,104, Jan. 12, 2011, Issue Notification.
U.S. Appl. No. 12/402,398, Jan. 24, 2011, Office Action.
U.S. Appl. No. 12/945,646, Jan. 20, 2011, Office Action.
U.S. Appl. No. 12/338,977, Jan. 19, 2012, Office Action.
U.S. Appl. No. 12/684,569, Jan. 27, 2012, Office Action.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 10/616,832, Jan. 26, 2011, Issue Notification.
U.S. Appl. No. 11/152,562, Jan. 26, 2011, Issue Notification.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 12/961,331, Feb. 1, 2013, Office Action.
U.S. Appl. No. 13/488,233, Feb. 5, 2013, Notice of Allowance.
U.S. Appl. No. 12/608,769, Feb. 10, 2012, Office Action.
U.S. Appl. No. 12/684,400, Feb. 13, 2012, Office Action.
U.S. Appl. No. 12/724,304, Feb. 10, 2012, Office Action.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/684,562, Feb. 16, 2012, Office Action.
U.S. Appl. No. 12/945,646, Feb. 21, 2012, Notice of Allowance.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 13/030,922, filed Feb. 18, 2011, Cummins.
U.S. Appl. No. 13/039,087, filed Mar. 2, 2011, Palermo et al.
U.S. Appl. No. 10/356,214, Feb. 23, 2011, Issue Notification.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 12/402,398, Mar. 13, 2013, Notice of Allowance.
U.S. Appl. No. 11/532,576, Mar. 16, 2011, Issue Notification.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 11/396,731, Mar. 22, 2011, Office Action.
U.S. Appl. No. 11/427,297, Mar. 21, 2011, Office Action.
U.S. Appl. No. 12/113,851, Mar. 29, 2012, Office Action.
U.S. Appl. No. 12/403,277, Apr. 3, 2012, Office Action.
U.S. Appl. No. 10/682,459, Apr. 1, 2011, Notice of Allowance.
U.S. Appl. No. 12/403,277, Mar. 31, 2011, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 10/147,774, Apr. 6, 2011, Issue Notification.
U.S. Appl. No. 12/114,091, Apr. 5, 2012, Office Action.
U.S. Appl. No. 12/684,542, Apr. 16, 2012, Office Action.
U.S. Appl. No. 12/122,603, Apr. 22, 2011, Office Action.
U.S. Appl. No. 11/744,089, Apr. 15, 2013, Office Action.
U.S. Appl. No. 11/852,190, Apr. 24, 2013, Office Action.
U.S. Appl. No. 12/846,642, Apr. 26, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/490,143, Apr. 29, 2013, Notice of Allowance.
U.S. Appl. No. 13/615,547, Apr. 12, 2013, Notice of Allowance.
U.S. Appl. No. 60/693,531, filed Jun. 24, 2005, Carly.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Jan. 13, 2010, Notice of Allowance.
U.S. Appl. No. 10/147,774, Oct. 26, 2009, Office action.
U.S. Appl. No. 10/264,306, Jan. 27, 2010, Office action.
U.S. Appl. No. 10/356,214, Jan. 13, 2010, Notice of Allowance.
U.S. Appl. No. 10/435,104, Jan. 20, 2010, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/541,083, Feb. 5, 2010, Notice of Allowance.
U.S. Appl. No. 10/616,832, Jan. 11, 2010, Notice of Allowance.
U.S. Appl. No. 10/541,083, Sep. 30, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/667,144, Nov. 23, 2009, Office action.
U.S. Appl. No. 10/682,459, Dec. 23, 2009, Office action.
U.S. Appl. No. 10/786,444, Jan. 14, 2010, Office Action.
U.S. Appl. No. 10/787,073, Feb. 17, 2010, Notice of Allowance.
U.S. Appl. No. 11/048,503, Jan. 11, 2010, Notice of Allowance.
U.S. Appl. No. 11/152,562, Mar. 31, 2010, Office action.
U.S. Appl. No. 11/344,891, Oct. 7, 2009, Office action.
U.S. Appl. No. 11/455,993, Feb. 17, 2009, Office action.
U.S. Appl. No. 11/455,993, Dec. 16, 2009, Office action.
U.S. Appl. No. 11/461,323, Apr. 5, 2010, Notice of Allowance.
U.S. Appl. No. 11/532,325, Jan. 5, 2010, Office action.
U.S. Appl. No. 11/532,576, Mar. 1, 2010, Office Action.
U.S. Appl. No. 11/532,576, Apr. 23, 2010, Office action.
U.S. Appl. No. 11/675,462, Dec. 10, 2009, Office action.
U.S. Appl. No. 11/767,818, Dec. 24, 2009, Office Action.
U.S. Appl. No. 11/767,818, Mar. 22, 2010, Office action.
U.S. Appl. No. 11/959,334, Aug. 19, 2009, Office action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 12/106,937, Nov. 18, 2009, Office action.
U.S. Appl. No. 12/106,928, Oct. 5, 2009, Office action.
U.S. Appl. No. 12/402,398, Mar. 9, 2010, Office Action.
U.S. Appl. No. 12/403,256, Dec. 16, 2009, Office Action.
U.S. Appl. No. 12/403,256, Mar. 30, 2010, Office action.
U.S. Appl. No. 29/296,370, Feb. 10, 2010, Issue Notification.
U.S. Appl. No. 13/308,227, filed Nov. 30, 2011, Yibarren.
U.S. Appl. No. 12/688,065, Apr. 26, 2012, Office Action.
U.S. Appl. No. 11/396,141, Apr. 30, 2013, Office Action.
U.S. Appl. No. 12/113,851, Apr. 27, 2011, Office Action.
U.S. Appl. No. 12/481,377, Apr. 28, 2011, Office Action.
U.S. Appl. No. 12/114,031, May 11, 2011, Office Action.
U.S. Appl. No. 12/143,020, May 11, 2011, Office Action.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 13/898,202, filed May 20, 2013, Walberg et al.
U.S. Appl. No. 11/344,891, May 15, 2013, Issue Notification.

(56) References Cited

OTHER PUBLICATIONS

U.S. Appl. No. 12/955,859, May 16, 2013, Office Action.
U.S. Appl. No. 13/488,233, May 15, 2013, Issue Notification.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 13/153,594, May 29, 2013, Office Action.
U.S. Appl. No. 13/791,829, May 29, 2013, Office Action.
U.S. Appl. No. 13/112,618, filed May 20, 2011, Gianotti et al.
U.S. Appl. No. 13/112,631, filed May 20, 2011, Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 12/608,773, Jun. 7, 2012, Office Action.
U.S. Appl. No. 13/026,989, Jun. 8, 2012, Office Action.
U.S. Appl. No. 12/338,977, Jun. 19, 2013, Office Action.
U.S. Appl. No. 13/112,631, Jun. 26, 2013, Office Action.
U.S. Appl. No. 12/481,377, Jun. 21, 2011, Office Action.
U.S. Appl. No. 11/344,891, Jun. 26, 2013, Issue Notification.
U.S. Appl. No. 12/106,928, Jun. 28, 2013, Office Action.
U.S. Appl. No. 12/106,937, Jun. 28, 2013, Office Action.
U.S. Appl. No. 12/402,398, Jun. 26, 2013, Issue Notification.
U.S. Appl. No. 12/941,809, Jul. 3, 2013, Office Action.
U.S. Appl. No. 12/961,331, Jul. 3, 2013, Office Action.
U.S. Appl. No. 10/786,444, Jul. 11, 2013, Notice of Allowance.
U.S. Appl. No. 13/615,547, Jul. 10, 2013, Issue Notification.
U.S. Appl. No. 12/114,091, Jul. 7, 2011, Office Action.
U.S. Appl. No. 12/945,646, Jul. 6, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 61/097,072, filed Sep. 15, 2008, Sibbitt, Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, Apr. 27, 2010, Notice of Allowance.
U.S. Appl. No. 10/147,774, Jun. 8, 2010, Office Action.
U.S. Appl. No. 10/264,306, Jun. 15, 2010, Office Action.
U.S. Appl. No. 10/356,214, May 13, 2010, Notice of Allowance.
U.S. Appl. No. 10/435,104, Jun. 2, 2010, Office Action.
U.S. Appl. No. 10/541,083, May 10, 2010, Notice of Allowance.
U.S. Appl. No. 10/616,832, May 12, 2010, Notice of Allowance.
U.S. Appl. No. 10/667,144, Jun. 22, 2010, Office Action.
U.S. Appl. No. 10/682,459, Apr. 28, 2010, Office Action.
U.S. Appl. No. 11/048,503, Apr. 26, 2010, Notice of Allowance.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,891, May 7, 2010, Office Action.
U.S. Appl. No. 11/390,586, Jul. 6, 2010, Office Action.
U.S. Appl. No. 11/396,141, May 4, 2010, Office Action.
U.S. Appl. No. 11/396,731, Jun. 29, 2010, Office Action.
U.S. Appl. No. 11/406,203, Jun. 18, 2010, Notice of Allowance.
U.S. Appl. No. 11/508,656, Dec. 9, 2009, Office Action.
U.S. Appl. No. 11/508,656, Mar. 25, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/852,190, Jun. 24, 2010, Office Action.
U.S. Appl. No. 11/958,295, May 25, 2010, Office Action.
U.S. Appl. No. 12/106,928, May 10, 2010, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, May 20, 2010, Office Action.
U.S. Appl. No. 12/135,858, Jul. 13, 2011, Office Action.
U.S. Appl. No. 10/435,104, Jul. 23, 2009, Notice of Allowance.
U.S. Appl. No. 10/669,313, Oct. 31, 2005, Office Action.
U.S. Appl. No. 11/113,549, Jul. 6, 2010, Office Action.
U.S. Appl. No. 11/959,334, Jul. 23, 2010, Notice of Allowance.
U.S. Appl. No. 12/403,277, Jul. 8, 2010, Office Action.
U.S. Appl. No. 12/955,859, Jul. 21, 2011, Office Action.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 60/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson et al.
U.S. Appl. No. 09/610,128, filed Jul. 5, 2000, Kerievsky.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/006,400, Aug. 2, 2010, Notice of Allowance.
U.S. Appl. No. 10/517,004, Aug. 3, 2010, Notice of Allowance.
U.S. Appl. No. 10/541,083, Aug. 17, 2010, Notice of Allowance.
U.S. Appl. No. 11/048,503, Jul. 30, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/757,108, Nov. 25, 2009, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 09/866,551, filed May 25, 2001, Ginn.
U.S. Appl. No. 10/638,115, Aug. 13, 2010, Notice of Allowance.
U.S. Appl. No. 10/787,073, Aug. 25, 2010, Notice of Allowance.
U.S. Appl. No. 12/403,256, Aug. 19, 2010, Notice of Allowance.
U.S. Appl. No. 11/396,731, Sep. 1, 2011, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/987,792, Sep. 17, 2012, Office Action.
U.S. Appl. No. 13/026,989, Sep. 16, 2011, Office Action.
U.S. Appl. No. 12/122,603, Sep. 23, 2011, Office Action.
U.S. Appl. No. 11/508,656, Aug. 30, 2010, Office Action.
U.S. Appl. No. 11/675,462, Aug. 31, 2010, Office Action.
U.S. Appl. No. 11/958,281, Sep. 2, 2010, Office Action.
U.S. Appl. No. 10/616,832, Sep. 20, 2010, Notice of Allowance.
U.S. Appl. No. 11/152,562, Sep. 16, 2010, Notice of Allowance.
U.S. Appl. No. 12/393,877, Sep. 29, 2011, Office Action.
U.S. Appl. No. 10/435,104, Oct. 5, 2010, Notice of Allowance.
U.S. Appl. No. 10/787,073, Sep. 15, 2010, Issue Notification.
U.S. Appl. No. 11/427,297, Sep. 15, 2010, Office Action.
U.S. Appl. No. 11/767,818, Sep. 30, 2010, Office Action.

(56) References Cited

OTHER PUBLICATIONS

U.S. Appl. No. 12/365,397, Sep. 13, 2010, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 10/264,306, Oct. 29, 2010, Notice of Allowance.
U.S. Appl. No. 10/356,214, Sep. 3, 2010, Notice of Allowance.
U.S. Appl. No. 10/682,459, Oct. 12, 2010, Office Action.
U.S. Appl. No. 11/406,203, Oct. 6, 2010, Issue Notification.
U.S. Appl. No. 11/508,715, Oct. 18, 2010, Office Action.
U.S. Appl. No. 11/532,576, Oct. 13, 2010, Notice of Allowance.
U.S. Appl. No. 11/958,281, Oct. 8, 2010, Office Action.
U.S. Appl. No. 12/114,031, Oct. 5, 2010, Office Action.
U.S. Appl. No. 12/403,277, Oct. 12, 2010, Office Action.
U.S. Appl. No. 10/667,144, Oct. 28, 2011, Notice of Allowance.
U.S. Appl. No. 12/945,646, Oct. 26, 2011, Office Action.
U.S. Appl. No. 12/106,928, Oct. 25, 2010, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 11/198,811, Oct. 20, 2010, Issue Notification.
U.S. Appl. No. 11/508,662, Oct. 26, 2010, Office Action.
U.S. Appl. No. 11/852,190, Nov. 1, 2010, Office Action.
U.S. Appl. No. 12/114,091, Oct. 27, 2010, Office Action.
U.S. Appl. No. 11/427,309, Nov. 15, 2010, Office Action.
U.S. Appl. No. 12/961,331, filed Dec. 6, 2010, Voss.
U.S. Appl. No. 12/966,923, filed Dec. 13, 2010, Cummins et al.
U.S. Appl. No. 10/147,774, Dec. 2, 2010, Notice of Allowance.
U.S. Appl. No. 10/517,004, Nov. 23, 2010, Issue Notification.
U.S. Appl. No. 10/541,083, Dec. 1, 2010, Issue Notification.
U.S. Appl. No. 11/959,334, Nov. 10, 2010, Issue Notification.
U.S. Appl. No. 12/114,031, Nov. 22, 2010, Office Action.
U.S. Appl. No. 12/403,256, Nov. 23, 2010, Issue Notification.
U.S. Appl. No. 11/048,503, Dec. 8, 2010, Issue Notification.
U.S. Appl. No. 12/393,877, Dec. 13, 2011, Office Action.
U.S. Appl. No. 12/941,809, Dec. 13, 2011, Restriction Requirement.
U.S. Appl. No. 12/955,859, Dec. 15, 2011, Office Action.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 12/897,358, filed Oct. 4, 2010, Carley.
U.S. Appl. No. 12/113,851, Dec. 16, 2010, Office Action.
U.S. Appl. No. 12/114,091, Dec. 17, 2010, Office Action.
U.S. Appl. No. 11/675,462, Dec. 22, 2011, Notice of Allowance.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/396,141, filed Aug. 21, 2013, Office Action.
U.S. Appl. No. 11/427,309, filed Sep. 25, 2013, Issue Notification.
U.S. Appl. No. 11/744,089, filed Aug. 8, 2013, Notice of Allowance.
U.S. Appl. No. 12/850,242, filed Aug. 6, 2013, Notice of Allowance.
U.S. Appl. No. 12/955,859, filed Aug. 1, 2013, Notice of Allowance.
U.S. Appl. No. 13/026,989, filed Aug. 23, 2013, Office Action.
U.S. Appl. No. 13/030,922, filed Jul. 18, 2013, Office Action.
U.S. Appl. No. 13/525,839, filed Jul. 15, 2013, Notice of Allowance.
U.S. Appl. No. 13/791,829, filed Oct. 8, 2013, Notice of Allowance.

* cited by examiner

SURGICAL STAPLER

CROSS REFERENCE TO RELATED APPLICATIONS

This application claims priority to Ireland Application No. S2004/0368 filed on May 25, 2004 and entitled "Surgical Stapler," which is hereby incorporated by reference in its entirety.

FIELD OF THE INVENTION

The present invention relates to methods and devices for closing a puncture wound in a liquid carrying vessel.

BACKGROUND OF THE INVENTION

A variety of surgical procedures require a puncture wound to be formed in a liquid carrying vessel, and upon completion of the procedure, the puncture wound must be closed in order to prevent loss of blood through the puncture hole. In certain cases, the wound can be closed by maintaining external pressure over the vessel until the puncture naturally seals. This procedure can take approximately 30 minutes with the length of time usually being greater if the patient is hypertensive or anticoagulated. The procedure can also be uncomfortable for the patient and involves costly professional time on the part of the hospital staff. Other pressure techniques such as pressure bandages, sandbags or clamps have been employed but these also involve ensuring the patient remains motionless for an extended period of time and is monitored to ensure the effectiveness of the procedure. Accordingly, a number of devices have been developed which provide an obstruction in the area of the puncture in order to prevent bleeding.

Such devices include, for example, collagen plugs which, when placed at the blood vessel opening, absorb body fluids, swell and affect a seal. Some plug like devices utilize an anchor that is positioned inside the vessel and a collagen plug that is positioned outside the vessel, thereby sandwiching the puncture to effect a closure. Surgical staples, clips, and other devices have also been used to close puncture wounds.

While these devices are typically effective, there remains a need for improved methods and devices for closing a puncture in a liquid-carrying vessel by stapling.

BRIEF SUMMARY OF THE INVENTION

The present invention generally provides methods and devices for closing a puncture wound in a liquid carrying vessel. In one exemplary embodiment, a surgical stapler is provided having a locator tube having proximal and distal ends with an inflation lumen extending through at least a portion thereof, and an inflatable member, such as an inflatable balloon, formed proximal to the distal end of the locator tube and in communication with the inflation lumen. The inflatable member is movable between a deflated position and an inflated position. The device also includes a staple applying apparatus that is slidably disposed on a portion of the locator tube proximal to the inflatable member. The staple applying apparatus is adapted to apply a surgical staple to seal a puncture wound in a liquid carrying vessel. The device can also include a guidewire entry port formed in a sidewall of the distal end of the locator tube at a location distal to the inflatable member, and a guidewire exit port formed in the proximal end.

The staple applying apparatus can have a variety of configurations, but in one embodiment it includes a sheath having a staple pusher slidably disposed therein and adapted to push a staple against an anvil disposed within a distal end of the staple applying apparatus, and a staple former slidably disposed around the staple pusher and the anvil and adapted to deform a staple. The sheath can have a distal end that is expandable from a closed position, in which the sheath is adapted to be deployed through a tissue tract, and an open position, in which the sheath is retracted relative to the staple pusher, staple former, and anvil. More preferably, the distal end of the sheath includes opposed cut-out portions formed therein to allow the sheath to move between the open and closed positions. The staple applying apparatus also preferably includes at least one staple having a central portion with an opening formed therein and disposed around the locator tube, and opposed legs extending distally from opposed ends of the central portion. In use, when the staple is pushed against the anvil by the staple pusher, the anvil is adapted to engage a portion of the opposed legs of the staple to move the legs a distance apart from one another such that the staple is adapted to be deployed into a liquid carrying vessel.

In other embodiments, the device can include a pressure relief valve coupled to the inflation lumen in the locator tube and adapted to regulate a pressure within the inflatable member. The device can also optionally include a position indicator formed on or in the locator tube that is effective to indicate a position of the inflatable member relative to a liquid carrying vessel. The position indicator can be, for example, a lumen extending through the locator tube and having a distal, blood inlet port formed adjacent to the inflatable member, and a proximal, blood outlet port. The blood inlet port is preferably formed just proximal to the inflatable member such that the inlet port will be positioned external to a liquid carrying vessel when the inflatable member is inflated and positioned against an internal surface of a liquid carrying vessel adjacent puncture wound.

In other embodiments of the present invention, a method for closing a puncture wound in a liquid carrying vessel is provided. The method includes the step of positioning an inflatable member within a liquid carrying vessel such that the inflatable member abuts a puncture wound formed in the vessel. In an exemplary embodiment, the inflatable member is positioned over a guidewire that is predisposed within the liquid carrying vessel. The method further includes the steps of positioning a distal end of a staple applying apparatus adjacent the puncture wound against an external surface of the liquid carrying vessel, deploying a surgical staple into the liquid carrying vessel such that the staple extends across the puncture wound, deflating the inflatable member and removing the locator tube from the liquid carrying vessel, and deforming the staple to close the puncture wound in the liquid carrying vessel. Prior to the step of positioning an inflatable member within a liquid carrying vessel, a locator tube can be advanced along a tissue tract through a puncture wound in a liquid carrying vessel to position a distal portion of the tube having the inflatable member formed thereon within the liquid carrying vessel. After the locator tube is advanced to position the inflatable member on the distal portion of the tube within the liquid carrying vessel, an external blood signal can be used to indicate the correct position of the inflatable member within the vessel. The inflatable member is preferably inflated and the locator tube is retracted until the inflatable member abuts the puncture wound in the liquid carrying vessel. Blood flow through a blood flow lumen formed on the locator tube can be used to indicate a position of the inflatable member relative to the liquid carrying vessel. Blood flowing preferably ceases when the inflatable member is positioned within the liquid carrying vessel and abuts the puncture wound internally.

In other aspects, the method can include, prior to the step of deploying a surgical staple, advancing a staple applying apparatus containing the surgical staple along a proximal portion of the locator tube to position a distal end of the staple applying apparatus at the puncture wound adjacent an external surface of the liquid carrying vessel. The staple applying apparatus preferably includes a sheath having a staple pusher slidably disposed therein, an anvil disposed distal of the pusher, and a staple former slidably disposed around the staple pusher and the anvil. In order to deploy the staple, the staple pusher is preferably advanced distally to push the staple against the anvil whereby the staple is moved to an open position. The staple is then further advanced distally to deploy opposed legs of the staple into the liquid carrying vessel. The step of deforming the staple can include the step of advancing the staple former further distally to deform the opposed legs of the staple around the anvil toward one another into a closed position. In yet another embodiment of the present invention, a method for closing a puncture wound in a liquid carrying vessel is provided and includes the steps of advancing a locator tube along a tissue tract through a puncture wound in a liquid carrying vessel to position a distal portion of the tube having an inflatable member formed thereon within the liquid carrying blood vessel, inflating the inflatable member on the locator tube, retracting the locator tube until the inflatable member abuts the puncture wound in the liquid carrying vessel, advancing a staple applying apparatus along a proximal portion of the locator tube to position a distal end of the staple applying apparatus at the puncture wound adjacent an external surface of the liquid carrying vessel, deploying a surgical staple into the liquid carrying vessel such that the staple extends across the puncture wound, deflating the inflatable member and removing the locator tube from the liquid carrying vessel, and deforming the staple to close the puncture wound in the liquid carrying vessel.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
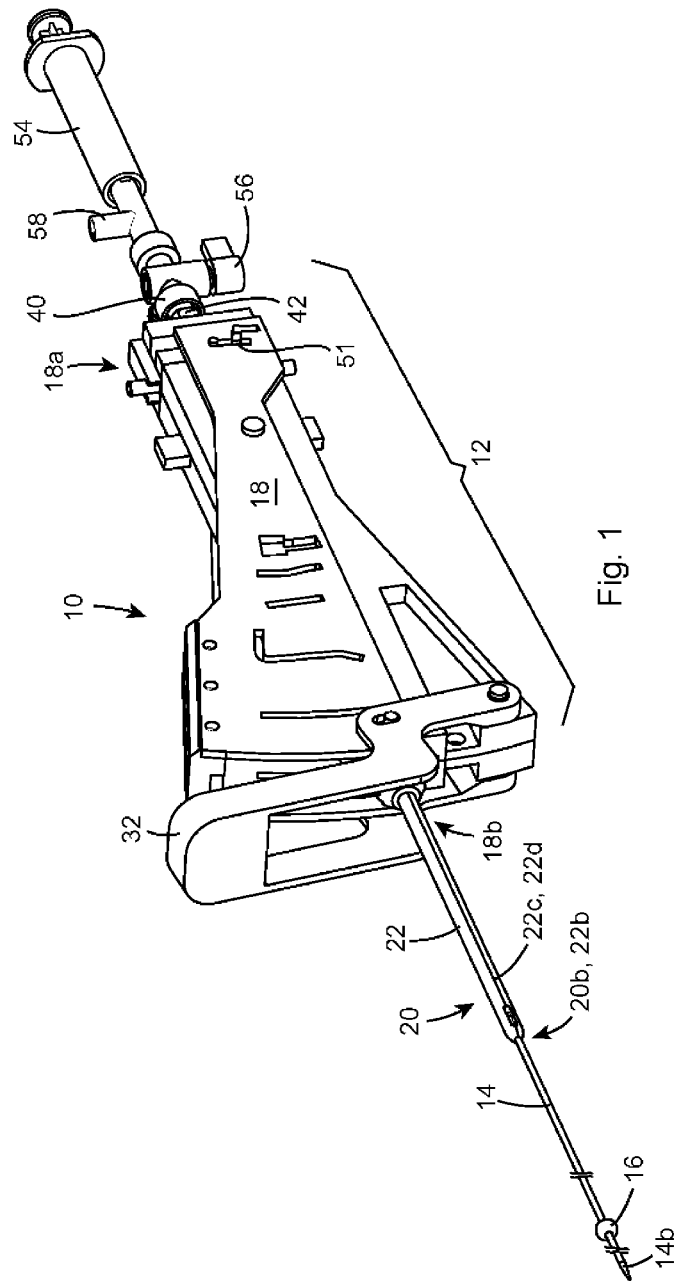
FIG. 1 is a perspective view of one embodiment of a surgical stapler having a staple applying apparatus slidably disposed around a locator tube in accordance with the present invention.

The present invention provides methods and devices for closing a puncture wound in a liquid carrying vessel. In one exemplary embodiment, shown in FIG. 1, a surgical stapler 10 is provided having a staple applying apparatus 12 that is slidably disposed around a locator tube 14. The locator tube 14 includes an inflatable member 16 formed thereon proximal to the distal end 14*b* thereof, and in use the inflatable member 16 is effective to locate a puncture wound in a liquid carrying vessel. In particular, the distal end 14b of the locator tube 14 can be inserted through a puncture wound in a vessel to position the inflatable member 16 within the vessel. The inflatable member 16 can then be inflated, and the locator tube 14 can be retracted until the inflatable member 16 abuts the internal surface of the vessel adjacent to the puncture wound. The staple applying apparatus 12 can then be moved along the locator tube 14 to position it against the external surface of the vessel adjacent the puncture wound, whereby a staple can be applied to close the puncture.

Figure 2:
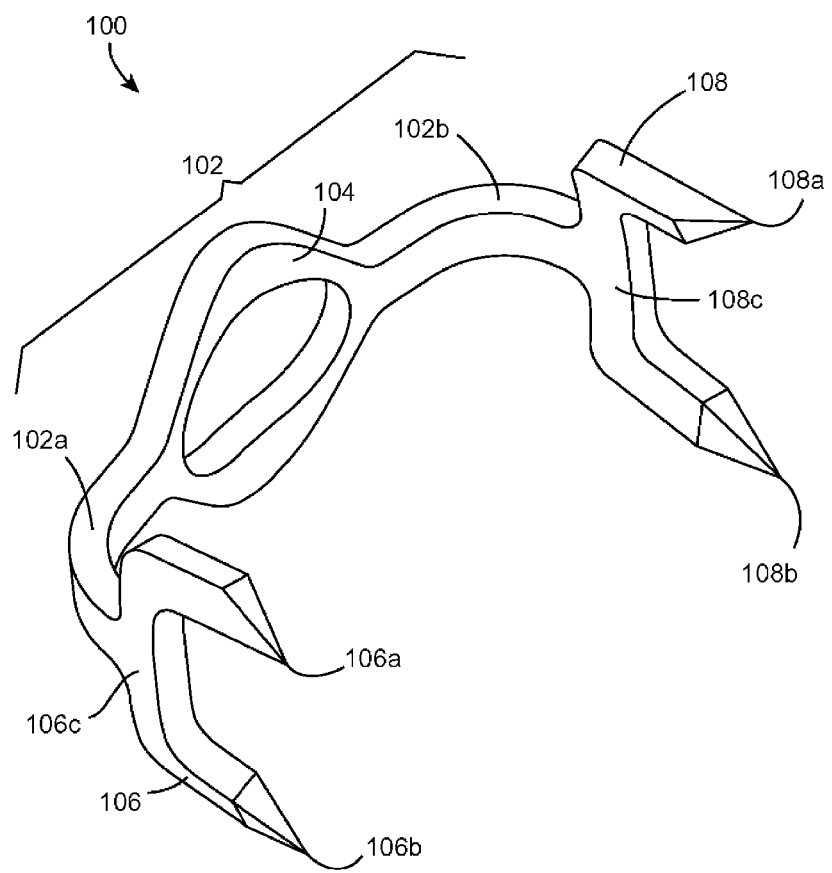
FIG. 2 is a perspective view of one embodiment of a staple in an open configuration according to the invention.
Figure 3:
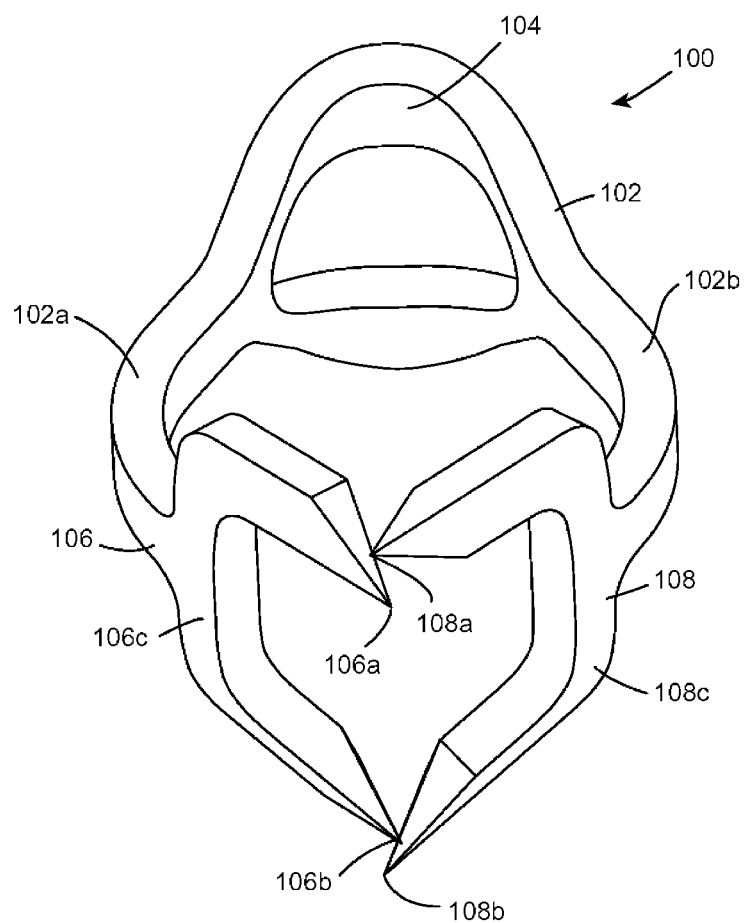
FIG. 3 is a perspective view of the staple shown in FIG. 2 in a closed configuration.
Figure 4:
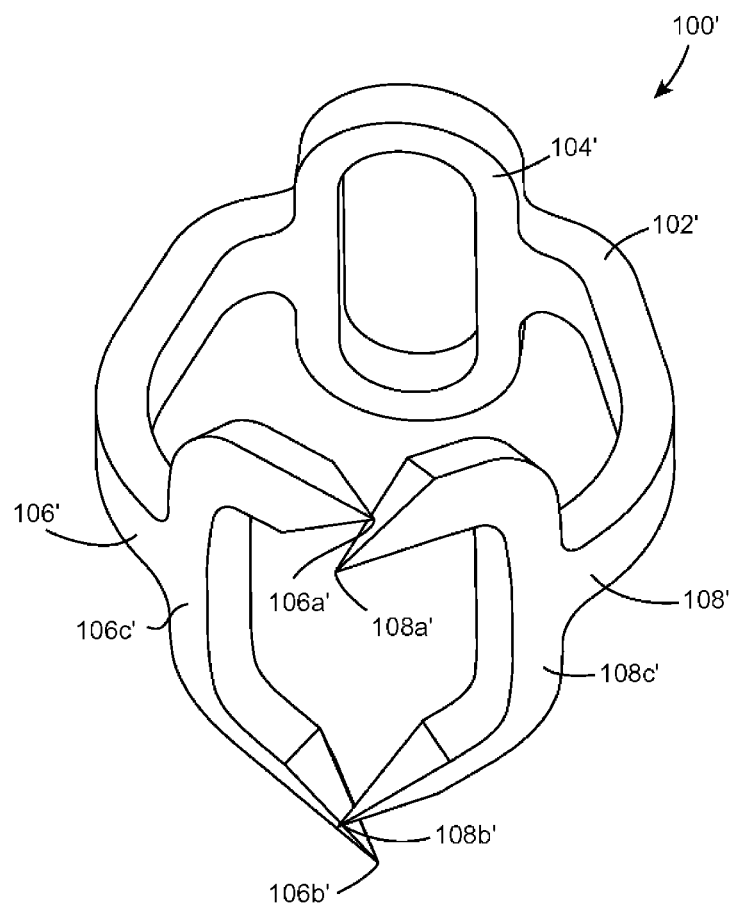
FIG. 4 is a perspective view of an alternative embodiment of a staple in a closed, pre-deployed configuration according to the invention.

At the outset, to facilitate understanding of the invention, it is necessary to describe an exemplary staple for using with the staple applying apparatus. A person skilled in the art will appreciate, however, that staples having a variety of shapes, sizes, and configurations can be used with the present invention. Referring to FIGS. 2-4, an exemplary staple 100 is shown and it is generally substantially U-shape and includes a base 102 with a loop section 104 and a pair of generally Y-shaped legs 106, 108 extending substantially perpendicularly from opposite ends 102a, 102b of the base 102. FIG. 2 illustrates the staple 100 in an open and ready to deploy configuration, in which the legs 106, 108 of the open staple 100 are bent approximately 90° relative to the base 102, and FIG. 3 illustrates the staple 100 in a closed configuration, in which the legs 106, 108 are bent toward one another. FIG. 4 shows an alternative embodiment for the closed post-deployed staple 100' where the loop section 104' has been changed in shape. To effect a greater compression of stapled tissue, the legs 106, 108, 106', 108' can include a penetrative portion 106a, 106b, 108a, 108b, 106a', 106b', 108a', 108b' adjacent the tip and a compressive structure 106c, 108c, 106c', 108c', which due to its increased height relative to that of the penetrative portion, spreads the compressive forces of the staple 100, 100' further along the length of the incision being closed. The compressive portion 106c, 108c, 106c', 108c' also provides a depth stop to avoid the tip 106a, 106b, 108a, 108b, 106a', 106b', 108a', 108b' penetrating too deeply into the tissue in which it is deployed. The staple 100, 100' is described in more detail in U.S. Publication No. 2004/0028502 entitled "Surgical Staple," filed on Jan. 22, 2003, and incorporated herein by reference in its entirety. A person skilled in the art will appreciate that the staple can have a variety of configurations, and moreover that the staple can be formed from a variety of materials. In an exemplary embodiment, the staple is bioabsorbable, and more preferably, by way of non-limiting example, the staple is formed from a magnesium alloy.

Referring back to FIG. 1, the staple applying apparatus 12 can have a variety of configurations, but it is preferably adapted to apply a surgical staple to seal a puncture wound in a liquid carrying vessel. In an exemplary embodiment, the staple applying apparatus 12 includes a handle housing 18 having a substantially rigid cylindrical shaft 20 extending therefrom. The cylindrical shaft 20 includes a staple opening and deployment mechanism 24 (FIGS. 5-10) for deploying a surgical staple to close a puncture wound, and the housing 18 includes components that are effective to actuate the staple opening and deployment mechanism 24.

Figure 5:
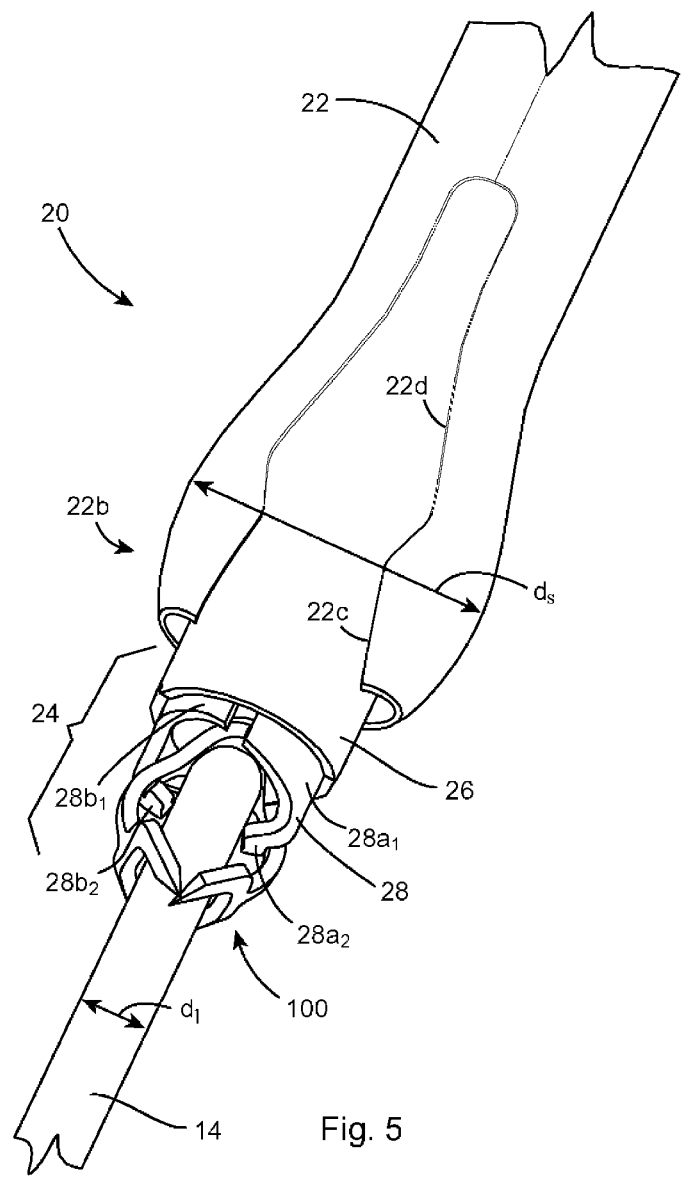
FIG. 5 is a perspective view of a portion of the staple applying apparatus shown in FIG. 1 having a sheath shown in a retracted position disposed around a former which is disposed around an anvil, and a surgical staple positioned between the anvil at a distal end of the former and around the locator tube, the apparatus being in a pre-deployed position.

The cylindrical shaft 20 is shown in more detail in FIGS. 5-10, and as shown, the shaft 20 is preferably formed from several cylindrical components. The outermost cylinder is a sheath 22, which preferably extends along the full length of the shaft 20. The sheath 22 is adapted to be disposed around the staple opening and deployment mechanism 24 during insertion of the device 12. Accordingly, while the shape and size of the sheath 22 can vary, in an exemplary embodiment the distal end 22b of the sheath 22 has an outer diameter $d_s$ (FIG. 5) that reduces at a distal-most end, preferably from approximately 4 mm to approximately 1.5 mm, which is the same as the outside diameter $d_l$ of the locator tube 13. Such a transition provides a smooth and blended profile for non-traumatic dilation of subcutaneous tissue during percutaneous insertion. Once the sheath 22 has been inserted through percutaneous tissue, it can be retracted to expose the staple opening and deployment mechanism 24. Thus, in order to facilitate retraction of the sheath 22, a distal end 22b of the sheath 22 can be splittable, and more particularly the sheath 22 can include one or more slits or openings formed therein that allow the distal end to spread apart when the sheath is retracted. In an exemplary embodiment, as shown in FIG. 5, the sheath 22 includes opposed slits 22c (only one opening is shown) that extend from the distal end 222b thereof and that have an enlarged proximal region 22d to prevent cracking or breaking of the sheath 22 as the sheath 22 is retracted. The slits 22c can vary in shape and size, but they should allow the sheath 22 to be retracted a sufficient distance to allow the staple opening and deployment mechanism 24 to be exposed.

Inside the sheath 22 is the staple opening and deployment mechanism 24, which includes a former component 26, a pusher 30, and an anvil 28. The former 26 extends cylindrically from the handle 18 to the distal tip 20b of the shaft 20 (FIG. 1), i.e., the distal tip 22b of the sheath 22, and it is preferably a generally elongate, cylindrical member that is used to protect the staple 100 in its pre-deployed position and secondly to close the staple 100 by deforming it against the anvil 28 that also extends from the handle 18 to the distal tip 20b of the shaft 20. The anvil 28 can vary in shape and size, but preferably it has a cylindrical shape with a distal end that is split axially to form two generally semicircular-sectioned extensions $28a_1$, $28b_1$. The extensions $28a_1$, $28b_1$ can each extend outward from the cylindrical body of the anvil 28, and can include a second portion $28a_2$, $28b_2$ that extends back inward toward the body 28 to form a tang, as shown in FIG. 5. The surface of the staple 100 will rest primarily against the tangs $28a_2$, $28b_2$ during the staple opening and closing processes, which will be discussed in more detailed below.

Figure 6:
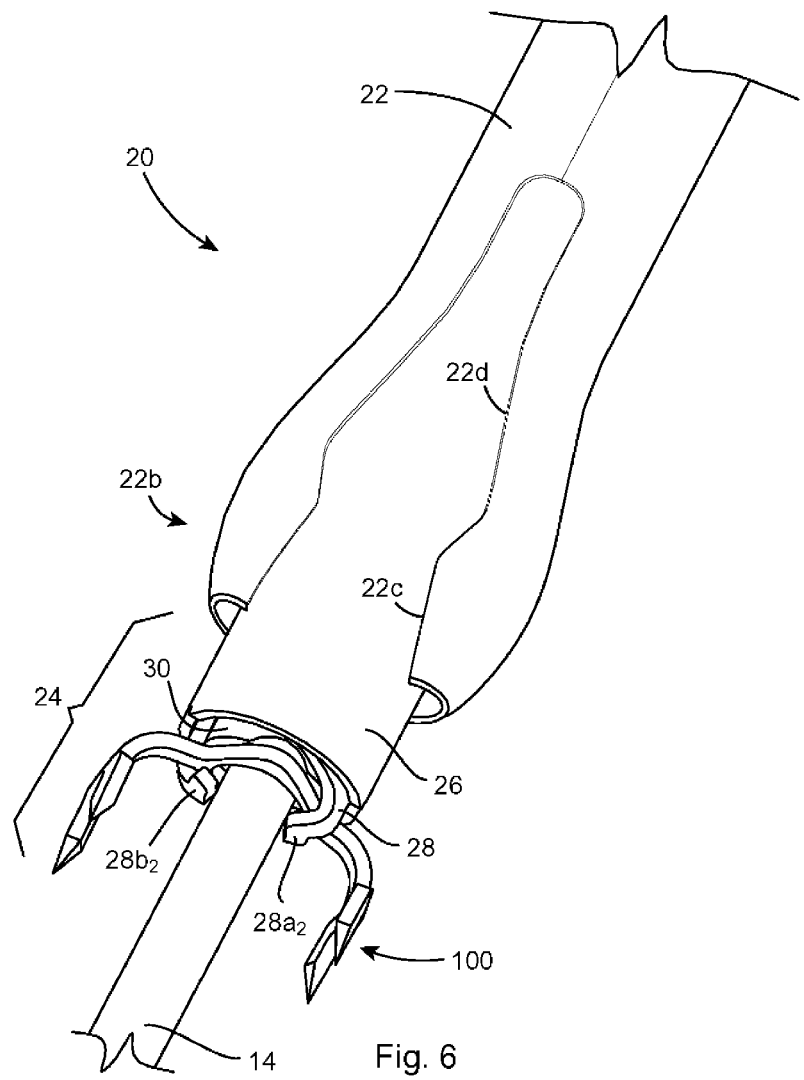
FIG. 6 is a perspective view of the staple applying apparatus shown in FIG. 5 with the staple advanced by a pusher disposed in the former into an open position in which the staple is ready to be deployed.
Figure 7:
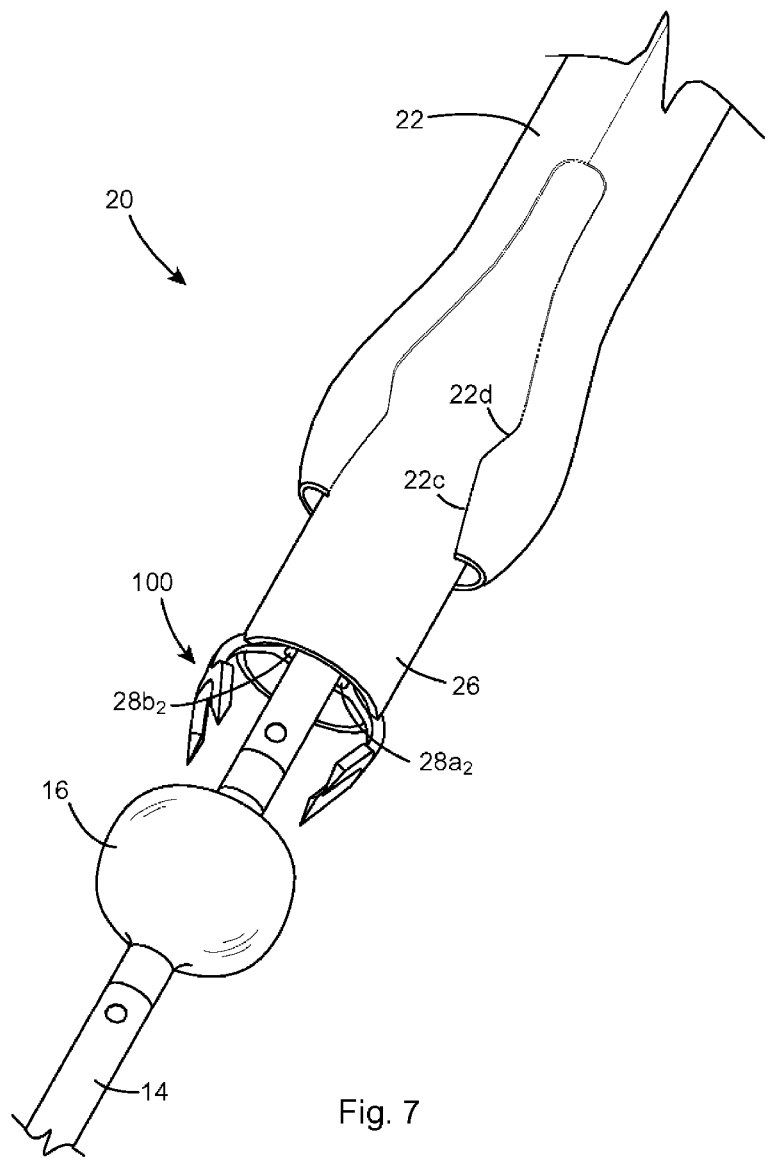
FIG. 7 is a perspective view of the staple applying apparatus shown in FIG. 6 with an inflatable member the locator in an inflated position, and with the staple partially deformed and ready to be fully-deployed.
Figure 8:
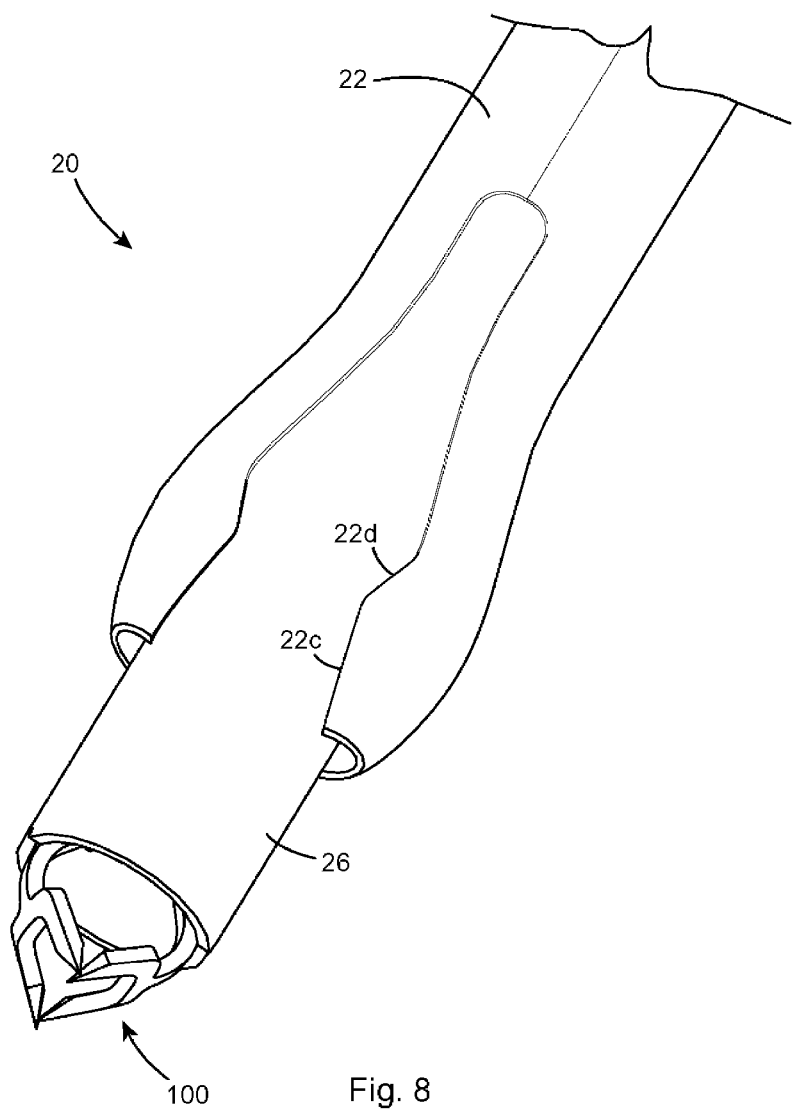
FIG. 8 is a perspective view of the staple applying apparatus shown in FIG. 7 with the locator tube removed, and with the staple fully deformed into a closed configuration.
Figure 9:
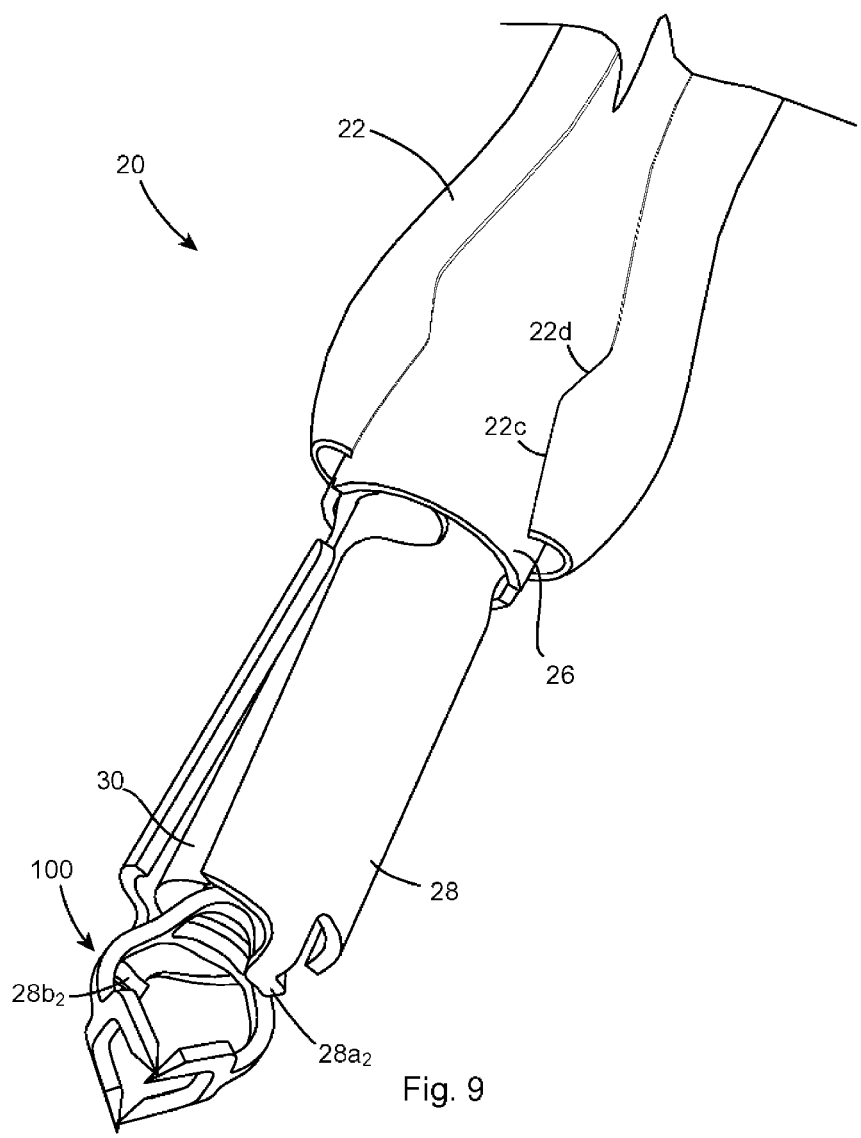
FIG. 9 is a perspective view of the staple applying apparatus shown in FIG. 8 with the former withdrawn and the anvil open to release the staple.
Figure 10:
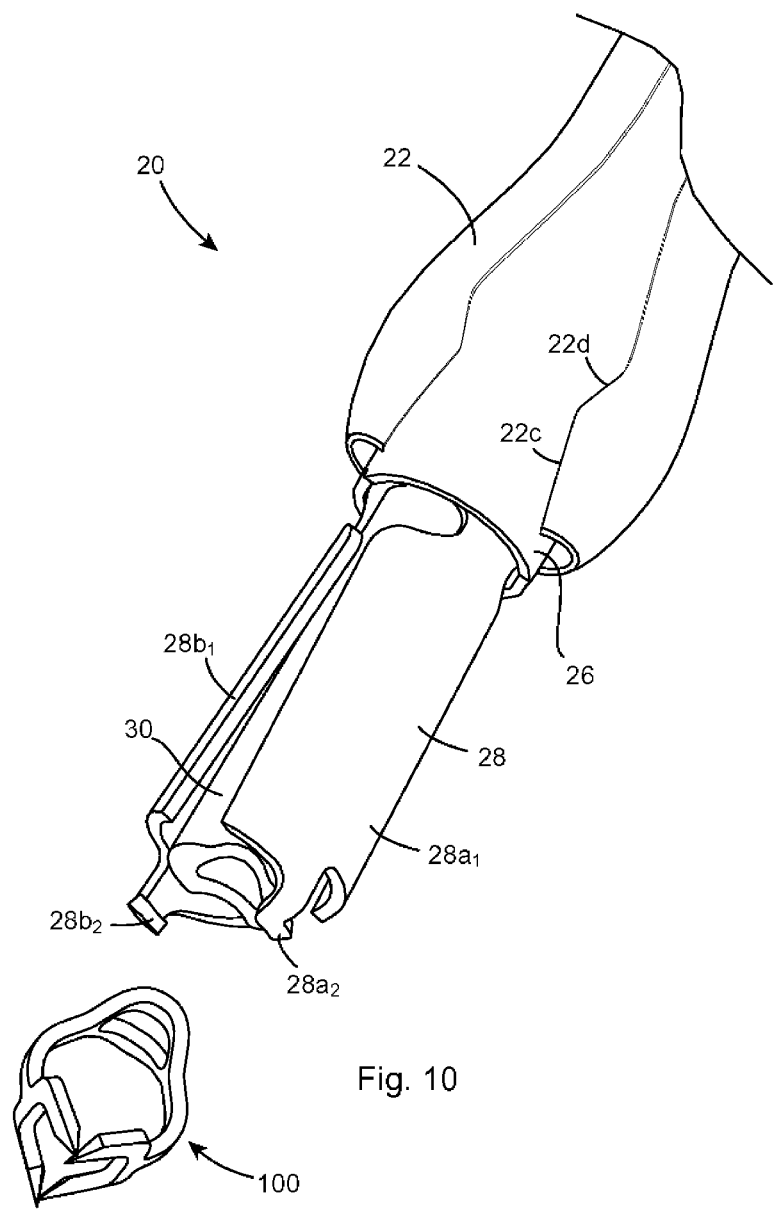
FIG. 10 is a perspective view of the staple applying apparatus shown in FIG. 9 with the staple released and the staple applying apparatus in the post-fire condition.

As noted above, the staple opening and deployment mechanism 24 also includes a pusher 30 that is disposed within the former 26, as shown in FIGS. 6, 9 and 10, and that is effective to advance the staple 100 toward the anvil 28 to deform the staple 100 from a pre-deployed, closed configuration (FIG. 3) to an open configuration (FIG. 2). In particular, the pusher 30 advances the staple 100 against the anvil tangs $28a_2$, $28b_2$ causing the arms 106, 108 of the staple 100 to deform into their open configuration. The pusher 30 also holds the staple 100 in position during deformation of the staple arms 106, 108 as the staple 100 is being closed, which can be achieved by moving the former 26 distally toward the anvil 28, thereby causing the legs 106, 108 to close. The pusher 30 further houses the locator tube 14, which extends from the proximal end 18b of the handle 18 (FIG. 1) through the shaft 20 and forward of the distal end 20b of the shaft 20. The locator tube 14 will be discussed in more detail below.

Figure 11:
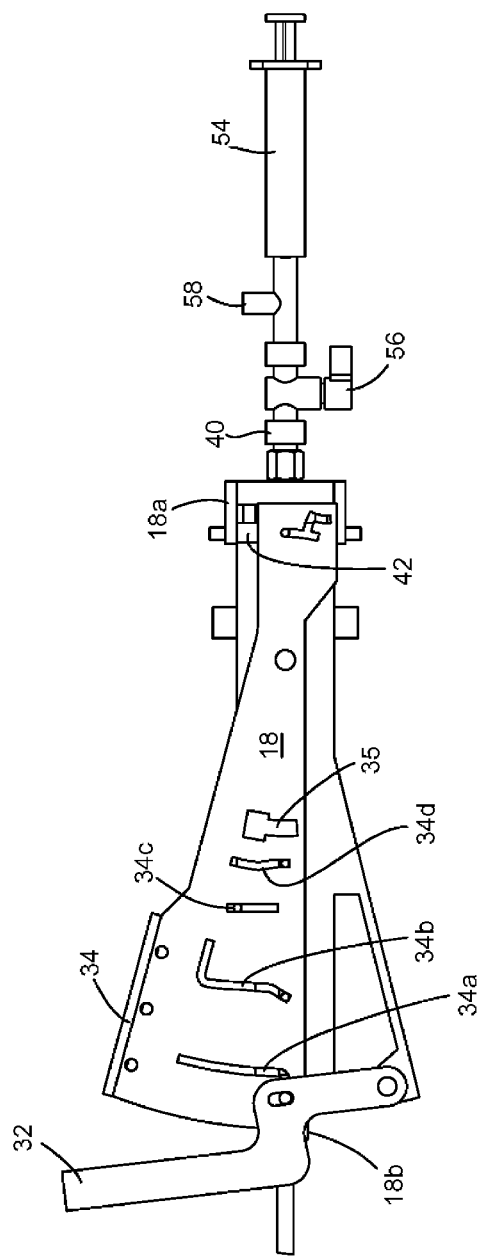
FIG. 11 is a side view of the staple applying apparatus shown in FIG. 1.
Figure 12:
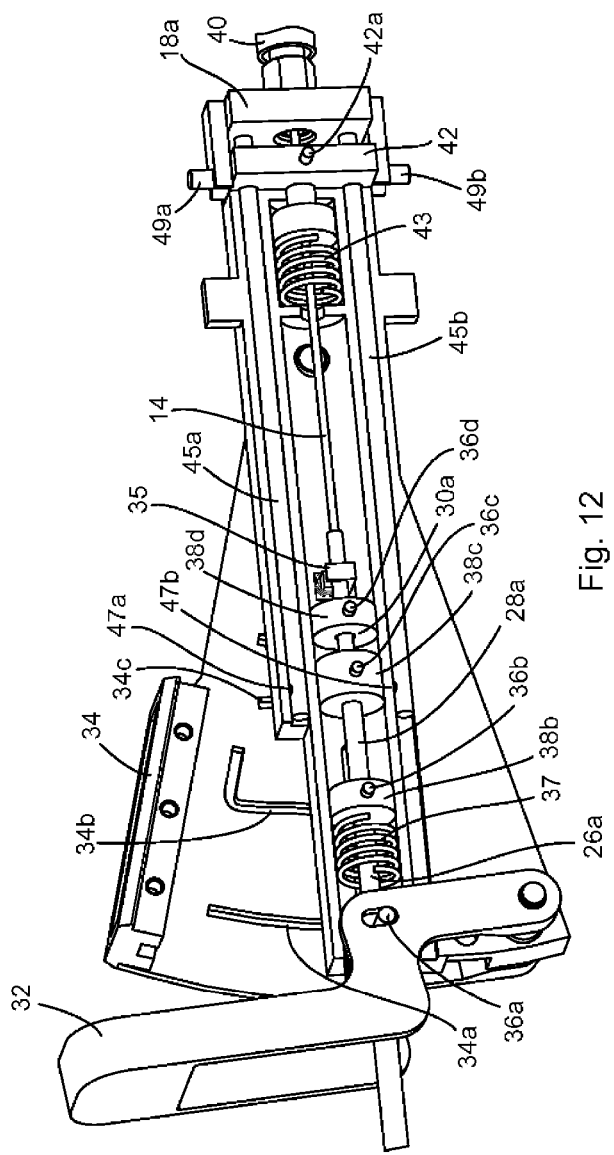
FIG. 12 is a side perspective view of the handle housing of the staple applying apparatus shown in FIG. 11 with the right side of the trigger and the right side of the handle housing removed.
Figure 13:
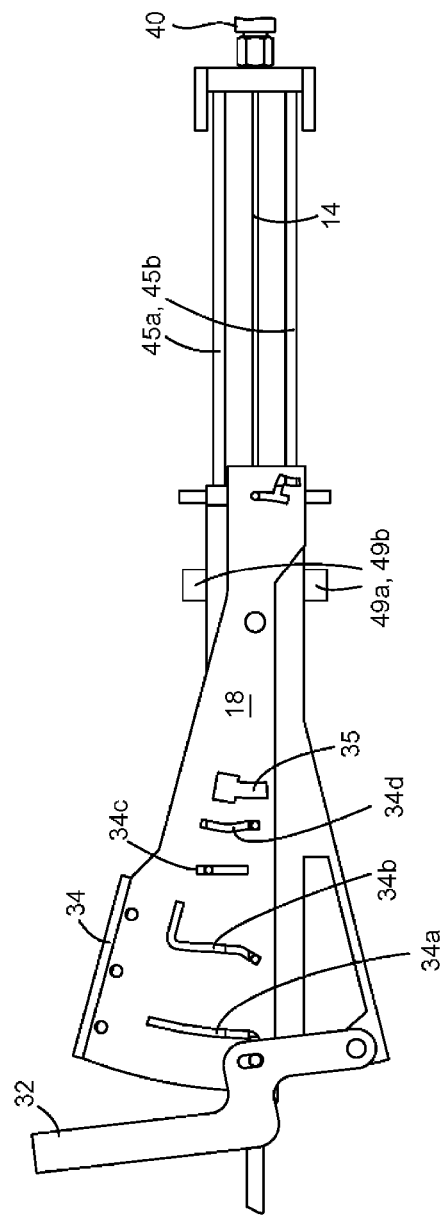
FIG. 13 is a side view of the staple applying apparatus shown in FIG. 12 advanced over the locator tube.

As previously mentioned, the shaft 20 extends from the handle housing 18, which contains components that are effective to actuate the staple opening and deployment mechanism 24. As shown in FIGS. 11-13, the handle housing 18 generally includes a sheath lever 32 that is effective to retract the sheath 22 to expose the staple opening and deployment mechanism 24, thus allowing a surgical staple 100 to be deployed into a vessel. Accordingly, the sheath lever 32 is attached to the proximal end (not shown) of the splittable sheath 22. The sheath 22 can, however, be retracted by a trigger 34 formed on the handle housing 18. The trigger 34 preferably has tracks 34a, 34b, 34c, 34d which engage with cylindrical pins 36a, 36b, 36c, 36d (FIG. 12) that extend from cylindrical bushes (only three bushes 38b, 38c, 38d are shown) formed on the proximal end (not shown) of the splitable sheath 22, the proximal end 26a of the former 26, the proximal end 28a of the anvil 28, and the proximal end 30a of the pusher 30, respectively. In use, the trigger 34 is effective to activate the pusher 30 to advance a staple 100 along the locator tube 14 until it comes into contact with the anvil 28, at which point the legs 106, 108 of the staple 100 are moved into an open position. The trigger 34, upon further activation, is also effective to move the staple 100 distally to penetrate a vessel, and then to move the former 26 distally to deform the staple 100 into a closed position, thereby closing a puncture wound in a vessel. The handle housing 18 is also effective to slidably receive the locator tube 14, which extends into the distal end 18b of the housing 18 and connects to a hub 40 formed on the proximal end 18a of the housing 18. The proximal end 18a, in turn, is connected to a movable flange 42 which, when disconnected from the handle 18, allows the locator tube 14 to be removed from the housing 18.

Figure 14:
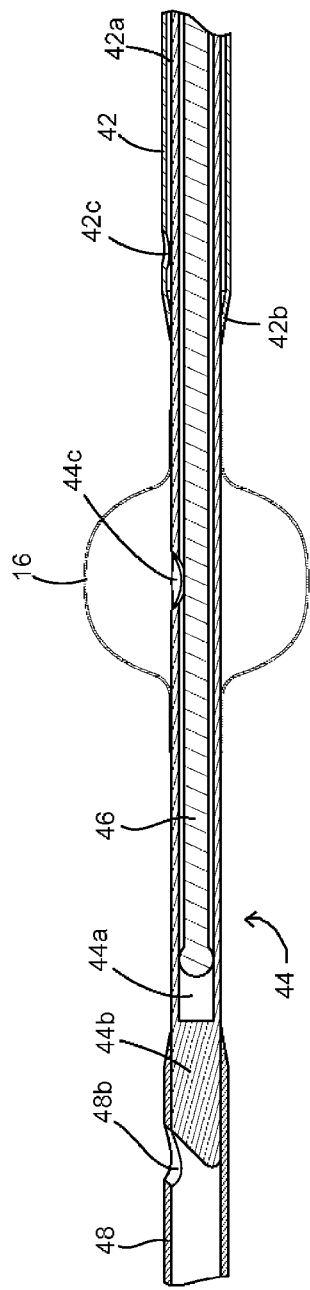
FIG. 14 is a cross-sectional view illustration of a distal portion of the locator tube shown in FIGS. 1 and 13.

An exemplary embodiment of a locator tube 14 for use with the surgical stapler 12 is shown in detail in FIG. 14, which illustrates the distal portion of the locator tube 14. The locator tube 14 can have a variety of shapes and sizes, but it preferably has a generally elongate cylindrical shape with one or more lumens extending therethrough between proximal and distal ends (only distal end 14b is shown in FIG. 14) thereof. In the illustrated embodiment, the locator tube 14 is formed from an outer tube 42 and an inner tube 44. The inner tube 44 extends distally beyond the outer tube 42, and it includes an inflation lumen 44a extending therethrough and having a side hole 44c that is in communication with an inflatable member, such as a balloon 16 as shown, for delivering fluid to the inflatable member 16. The inflatable member 16 is preferably disposed on the inner tube 44 at a location that is proximal to the distal end 44b thereof. The inflation lumen 44a terminates proximal to the distal end 44b of the inner tube 44 to prevent fluid flowing therethrough from exiting the locator tube 14. The inflation lumen 44a can also include a core wire 46 extending therethrough and adapted to add rigidity and stiffness to the tube 14.

The outer tube 42, which is disposed around the inner tube 44, terminates proximal to the inflatable member 16, and it also defines a lumen 42a extending therethrough. The lumen 42a in the outer tube 42, however, is configured to receive blood flow therethrough for indicating a position of the inflatable member 16. In particular, a blood entry port 42c is formed in the outer tube 42 adjacent the distal end 42b thereof for allowing blood to flow through lumen 42a in the outer tube 42, e.g., within a channel formed between the outer tube 42 and the inner tube 44. The lumen/channel 42a extends to a blood exit port 42d (shown in FIG. 16) that is formed in the outer tube 42 at a location that is just distal to the distal end 22b of the shaft 22 of the staple applying apparatus 12. As a result, when the locator tube 14 is positioned within a blood vessel, blood can flow into the blood entry port 42c, through the lumen/channel 42a, and out the blood exit port 42d to indicate that the locator tube 14, and in particular the inflatable member 16, is positioned within the blood vessel. The blood exit port 42d is also preferably positioned such that, when the inflatable member 16 is inflated and the locator tube 14 is retracted until the inflatable member 16 abuts the inner surface of the blood vessel, the blood exit port 42d is located outside of the blood vessel. As a result, blood will not flow through the lumen/channel 42a indicating that the inflatable member 16 is properly positioned within the blood vessel against the puncture wound.

In another embodiment, the locator tube 14 can include a guide lumen 48 extending therethrough for receiving a guide wire 50. While the guide lumen 48 can be formed at a variety of locations on the locator tube 14, in the embodiment shown in FIG. 14, the guide lumen 48 is formed from a single lumen tube that extends from the distal end 44b of the inner tube 44 of the locator tube 14 and that includes an open distal tip 48a (FIG. 15) and a side hole 48b formed at the proximal end thereof. In use, a guide wire 50 can be placed through the single lumen tube 48 to guide the locator tube 14 through a puncture and into a blood vessel, as will be discussed in more detail blow.

As previously indicated and shown in FIGS. 11-13, the proximal end 14a of the locator tube 14 is connected to the hub 40 formed on the proximal end 18a of the handle housing 18. The hub 40 can be attached to the proximal end 18a, and one or more rigid guide tubes 45a and 45b can extend from the proximal end 18a and through the flange 42 and the handle 18. Once the proximal end 18a is disconnected from the flange 42, which is connected to the handle 18, it is held in position and the handle 18 is advanced along the guide tube(s) 45a and 45b and locator tube 14 until notches 47a and 47b at the distal end of the tube(s) engage with pins 49a and 49b within the handle 18 which are propelled by springs into these notches.

Referring to FIGS. 1 and 11, in order to inflate the inflatable member 16, a syringe 54 can be coupled to the hub 40 to deliver fluid and/or gas to the inflatable member 16 to cause it to expand from a closed position to an open position. A stop cock 56 can also be formed on the hub 40 to open and close fluid flow through the hub 40, and a pressure relief valve 58 can be coupled to the hub 40 for regulating the pressure within the inflatable member 16. In an exemplary embodiment, the pressure relief valve 58 allows leakage to occur once a predetermined pressure, such as 4 Bar, has been achieved in the inflatable member 16.

Figure 15:
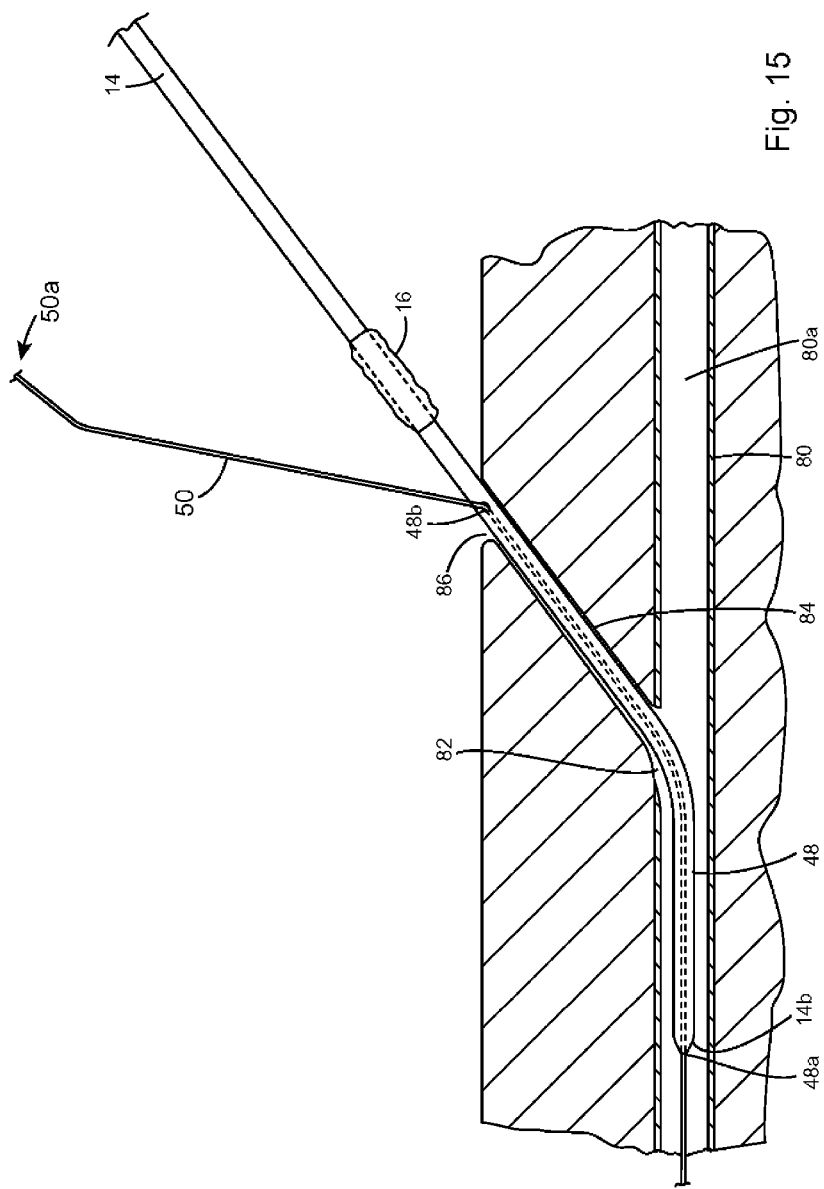
FIG. 15 is a side, partially cross-sectional view of method for using the surgical stapler of FIG. 1, showing the locator tube disposed around a guidewire and having a deflated balloon positioned outside an arterial lumen.
Figure 16:
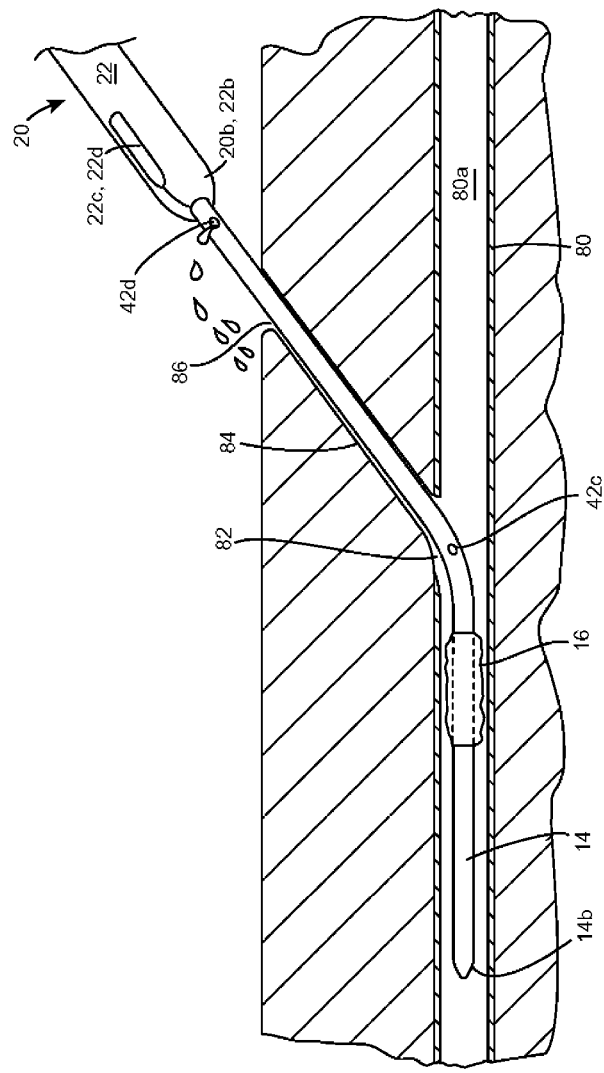
FIG. 16 is a side, partially cross-sectional view of the locator tube shown in FIG. 15 with the deflated balloon positioned inside the arterial lumen.

FIGS. 15-26 illustrate the surgical stapler 10 in use. In general, once an investigational or therapeutic procedure has been completed a guidewire 50 which is positioned within the artery 80 and extends through the arterial puncture hole 82, the tissue tract 84 and skin puncture 86, will be left in position. Referring to FIG. 15, the locator tube 14, and in particular the guidewire tube 48 that forms the distal portion of the locator tube 14, is advanced over the exposed proximal tip 50a of the guidewire 50 until the guidewire 50 exits the locator tube 14 through the guidewire exit hole 48b formed in the wall of the guidewire tube 48 on the distal side of the balloon 16. The locator tube 14 continues to be advanced along the guidewire 50 through the puncture hole 86 in the skin, through the tissue tract 84 and through the puncture hole 82 in the artery 80 and into the arterial lumen 80a. Advancing the locator tube 14 along the guidewire 50 will stop when the guidewire exit hole 48b aligns with the skin puncture, as shown. At this point the guidewire 50 may be removed and discarded. The locator tube 14 preferably has a length that is sufficient to ensure that the locator tube 14 enters the artery 80 prior to removal of the guidewire 50. The locator tube 14, and more particularly the guidewire tube 48 portion of the locator tube 14, also preferably has sufficient stiffness and/or rigidity to guide the locator tube 14 into the artery, in the absence of the guidewire 50, until the blood entry hole 42c positioned on the proximal side of the balloon 16 enters the arterial lumen 80a causing blood to enter and travel in a proximal direction through the lumen 42a until it exits at the blood signal hole 42d, as shown in FIG. 16. This signal confirms correct position of the balloon 16 within the arterial lumen 80a.

Figure 17:
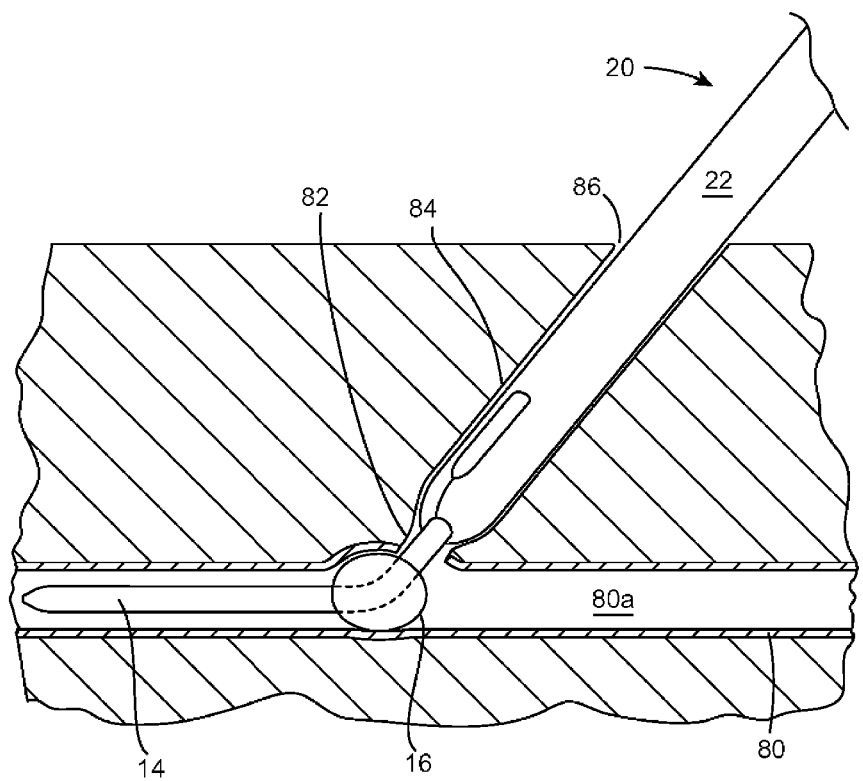
FIG. 17 is a side, partially cross-sectional view of the locator tube shown in FIG. 16 with the balloon inflated within the arterial lumen, and having the distal end of the staple applying apparatus shown in FIG. 1 positioned at the arterial puncture site.

As shown in FIG. 17, the balloon 16 is then inflated. In particular, the syringe 54 containing fluid is connected to the hub 40, via the pressure relief valve and stopcock. The stopcock 56 is turned to its open position, and fluid is injected into the locator tube 14 and balloon 16 until the pressure relief valve 58 indicates that the correct balloon pressure has been reached. Leakage preferably occurs at the pressure valve 58 once a maximum pressure, e.g., 4 Bar, has been reached. At this point the stopcock 56 is turned to a closed position thereby ensuring that the balloon 16 remains inflated. The handle 18 to which the locator tube 14 is attached is moved back causing the locator tube 14 and the inflated balloon 16 to move back intra-arterially towards the puncture hole 82. When the balloon 16 reaches the puncture hole 82, resistance will be felt as the balloon 16 cannot travel any further, signalling the correct position of the balloon 16. In addition the balloon 16 can act as a tamponade ensuring a reduction in blood loss through the puncture hole 82.

If the balloon 16 is correctly located against the endo-arterial surface at the puncture site 82, the blood inlet hole 42c will be external to the artery 80 and the signalling will have ceased, confirming the correct location of the balloon 16. Adversely, if resistance to withdrawing the balloon 16 is felt and the signal continues, this will indicate that the balloon 16 may be falsely anchored within the artery lumen 80a and is incorrectly positioned.

At this point the shaft 20 must be advanced along the locator tube 14 to a point where the distal tip 20b of the shaft 20 is juxtaposition on the arterial puncture hole 82, as is also shown in FIG. 17. This is done by releasing the proximal end 18a at the proximal end of the handle 18, holding it in a fixed position and advancing the handle 18 and rigid shaft 20 distally along the rigid guide tube(s) 45a and 45b and the locator tube 14 until the handle 18 locks into a predefined position onto the rigid tube(s) 45a and 45b and will advance no further. The handle 18 preferably advances along locator tube 14 and rigid guide tube(s) 45a and 45b slide rails until rail lock pins 49a and 49b engage with notches 47a and 47b in the guide tube preventing the handle 18 from moving forward any further. When fully advanced, the distal tip 22b of the sheath 22 is preferably positioned about 3 mm to 10 mm back from the proximal surface of the balloon 16. This allows space for the opening of the staple 100 with minimal risk of damage to the artery 80 at the puncture site 82 due to contact with the moving staple legs 106, 108.

Figure 18:
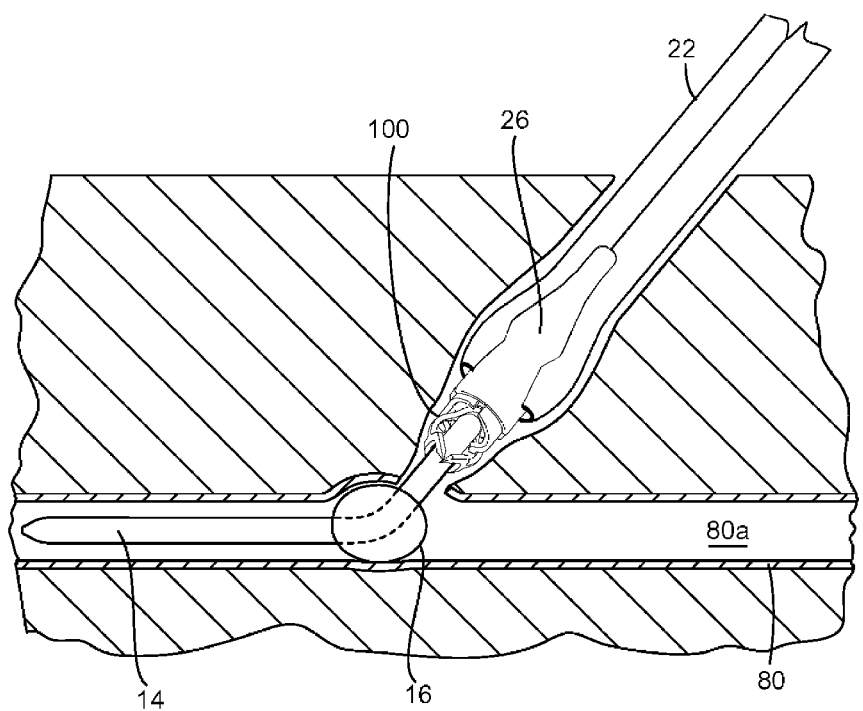
FIG. 18 is a side, partially cross-sectional view of the locator tube and staple applying apparatus shown in FIG. 17 with the sheath and former withdrawn to expose the staple.
Figure 19:
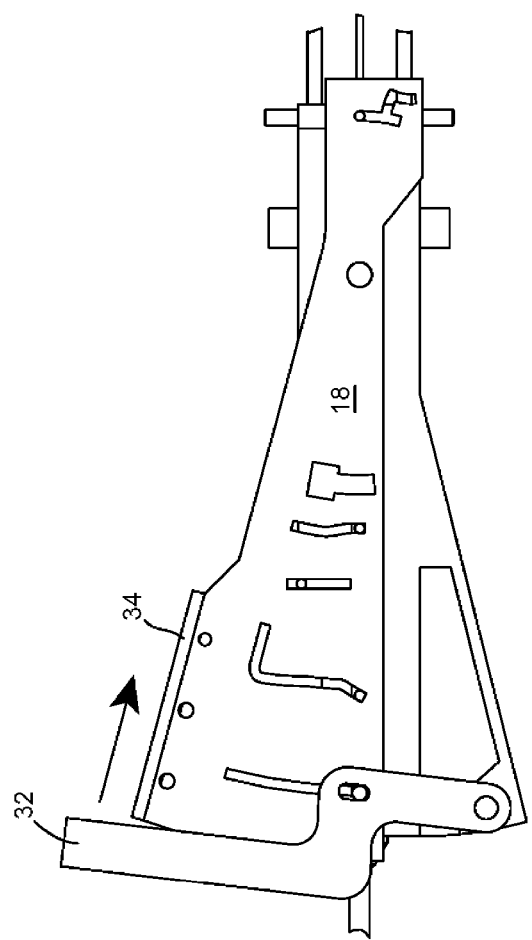
FIG. 19 is a side view of the staple applying apparatus shown in FIG. 11 with the sheath lever activated.

Prior to opening and deployment of the staple 100, the splitable sheath 22 must be withdrawn and the former 26 retracted to expose the staple 100 as shown in FIG. 18. Activation of the trigger 34 is not possible until the sheath lever 32 is back to its stopped position. Pulling back on the sheath lever 32, in a direction indicated by the arrow shown in FIG. 19, retracts the splitable sheath 22. This has the effect of pulling the reduced diameter section of the sheath 22 against the cylindrical profile of the former 26. As a result, the sheath 22 splits at the distal tip and is retracted over the former 26. The former 26 and sheath 22 are further retracted together so as to expose the anvil 28 and the staple 100, which is in a pre-deployed configuration such that the locator tube 14 extends through the cylindrical base 102 and the legs 106, 108 are bent inward toward one another.

Figure 20:
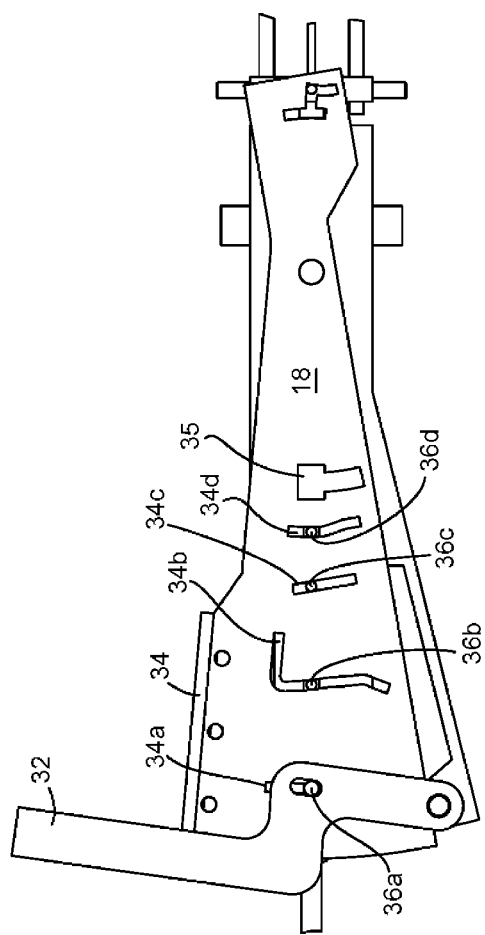
FIG. 20 is a side view of the staple applying apparatus shown in FIG. 19 with the trigger semi-deployed.
Figure 21:
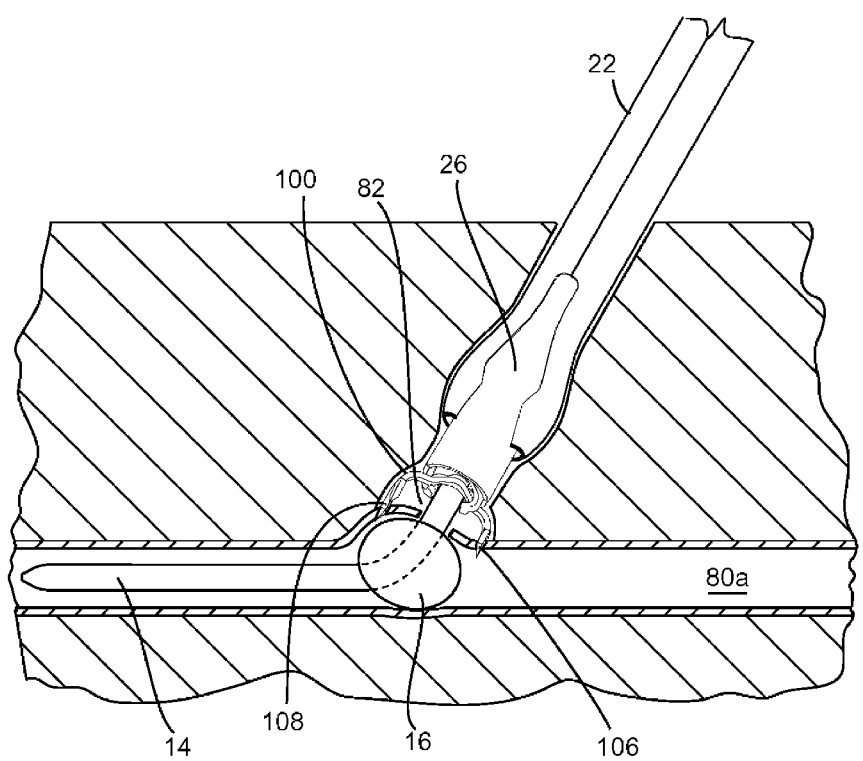
FIG. 21 is a side, partially cross-sectional perspective view of the locator tube and apparatus shown in FIG. 18 with the open staple penetrated into the arterial wall.
Figure 22:
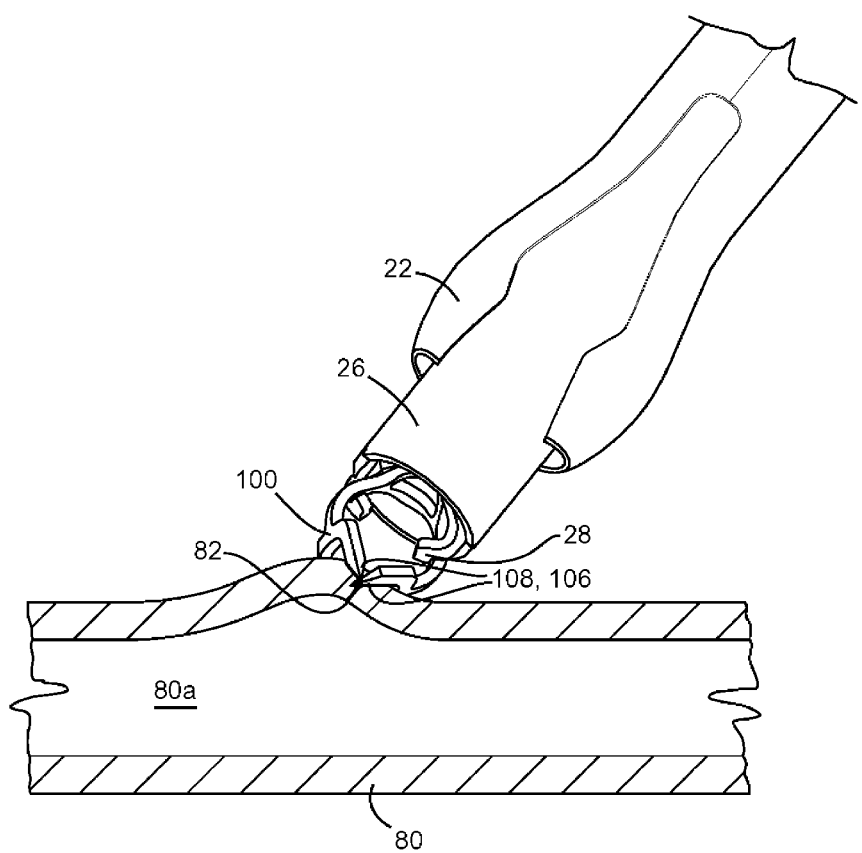
FIG. 22 is a side, partially cross-sectional perspective view of the locator tube and apparatus shown in FIG. 21 with the locator tube withdrawn and the staple deformed and deployed into the arterial wall to close the puncture.

The trigger 32 is then advanced to a first stop, as shown in FIG. 20. During this movement of the trigger 32, the pins 36a, 36b, 36c, 36d that extend from the cylindrical bush (only bushes 38b, 38c, and 38d are shown in FIG. 12) that is attached to the proximal end of the former 26, anvil 28, and pusher 30 engage with tracks 34a, 34b, 34c, 34d that are cut into each side of the handle assembly 18 (FIGS. 12 and 20). The shape of each track 34a, 34b, 34c, 34d with which the pins 36a, 36b, 36c, 36d engage dictates the axial movement of the cylindrical bush (38b, 38b, 38d in FIG. 12) to which the pins 36a, 36b, 36c, 36d are attached. During this part of the cycle the pusher 30 is advanced forward to open the staple 100, as shown in FIG. 21. In particular, the pusher 30 has advanced the loop 104 of the staple 100 forward so that the arms 106, 108 of the staple 100 firstly abut the anvil tangs 28a, 28b then cause the arms 106, 108 of the staple 100 to bend outward thus displacing the staple legs 106, 108 away from each other and away from the locator tube 14. As the staple arms 106, 108 bend open they engage with slots (not shown) in the former 26 so as to ensure they remain in correct alignment. Opening of the staple 100 continues until the staple legs 106, 108 are approximately 90 degrees to the staple base 102 or loop 104. Once the staple 100 is fully open the trigger 34 on the handle 18 continues to advance. A latch 51 (FIG. 1) at the proximal end of the trigger 34 is released allowing a compression spring 43 (FIG. 12) to push the moveable flange 42, that is attached to the proximal end 18a which is attached to the locator tube 14, in a proximal direction. This in turn causes the balloon 16 and staple 100 to advance toward each other until the staple legs 106, 108 have punctured the arterial wall 80. As the trigger 34 continues to be advanced the former 26 is moved forward against the staple arms 106, 108 causing them to be deformed around the anvil tangs 28a, 28b and the staple legs 106, 108 to bend and move toward each other. The staple 100 is now in a semi-deployed configuration and attached to the wall of the artery 80, as shown in FIG. 22. Once the staple 100 has been partially deformed toward its closed position, the trigger 34 reaches a mechanical stop and remains in the first, partially activated position shown in FIG. 20. A mechanical interlock 35 (FIG. 12) prevents any further advancement until the locator tube 14 has been withdrawn from the artery 80 through the shaft 20 and handle 18.

Figure 23:
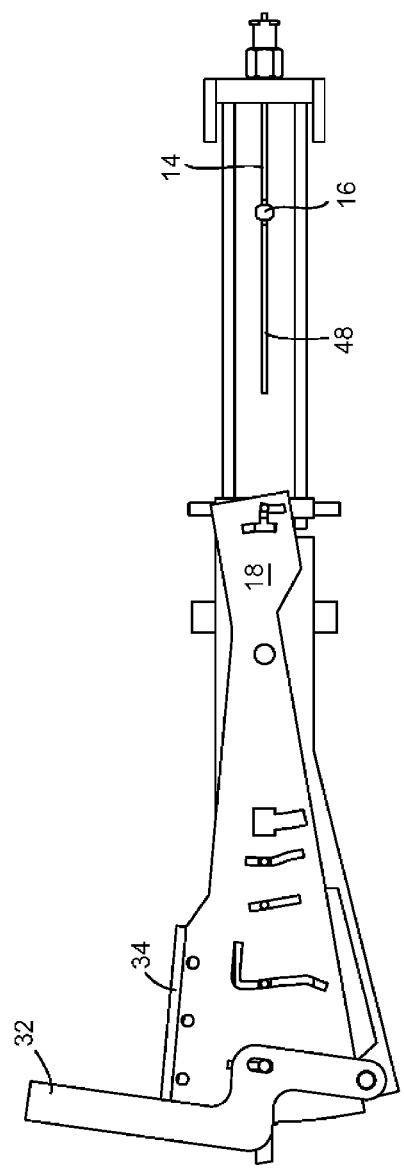
FIG. 23 is a side view of the staple applying apparatus shown in FIG. 20 with the locator tube fully withdrawn.

The locator tube 14 is withdrawn after deflating the balloon 16. This is done by turning the stopcock 56 to an open position and using the syringe 54 to deflate the balloon 16. Once deflated the stopcock 56 is turned back to the closed position or to a locked position, and the locator tube hub 40 is disconnected from the proximal end 18a on the proximal end of the handle housing 18. The locator tube 14 is fully withdrawn from the artery 80 and the device 12, as shown in FIGS. 22 and 23. Alternatively, the moveable flange 42, which is now engaged with the handle 18, may be disengaged and removed. As the locator tube 14 is attached to the slide assembly via the hub 40 at the proximal end 18a it will also be fully withdrawn from the device 12.

Figure 24:
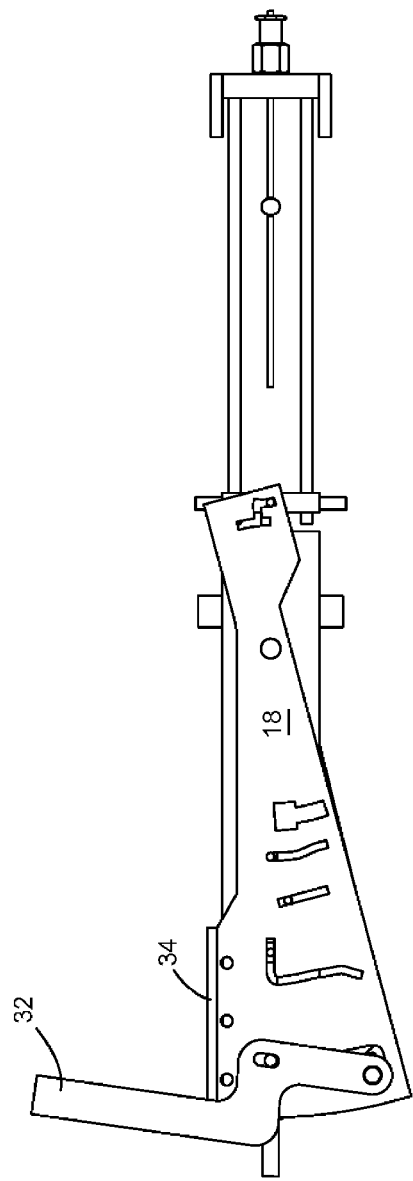
FIG. 24 is a side view of the staple applying apparatus shown in FIG. 23 with the trigger fully deployed.

Once the locator tube 14 is withdrawn from the device 12, the trigger interlock 35 disengages allowing the trigger 34 to be advanced further. The trigger 34 may then be fully deployed, as shown in FIG. 24, causing the former 26 to advance fully over the staple 100 while the pusher 30 is moving back simultaneously to form it to its closed position around the puncture hole 82 so as to effect closure of the puncture wound 82. Such a technique also reduces the applied stress on the staple material, and it achieves a staple configuration with a tighter and stronger closure.

Figure 25:
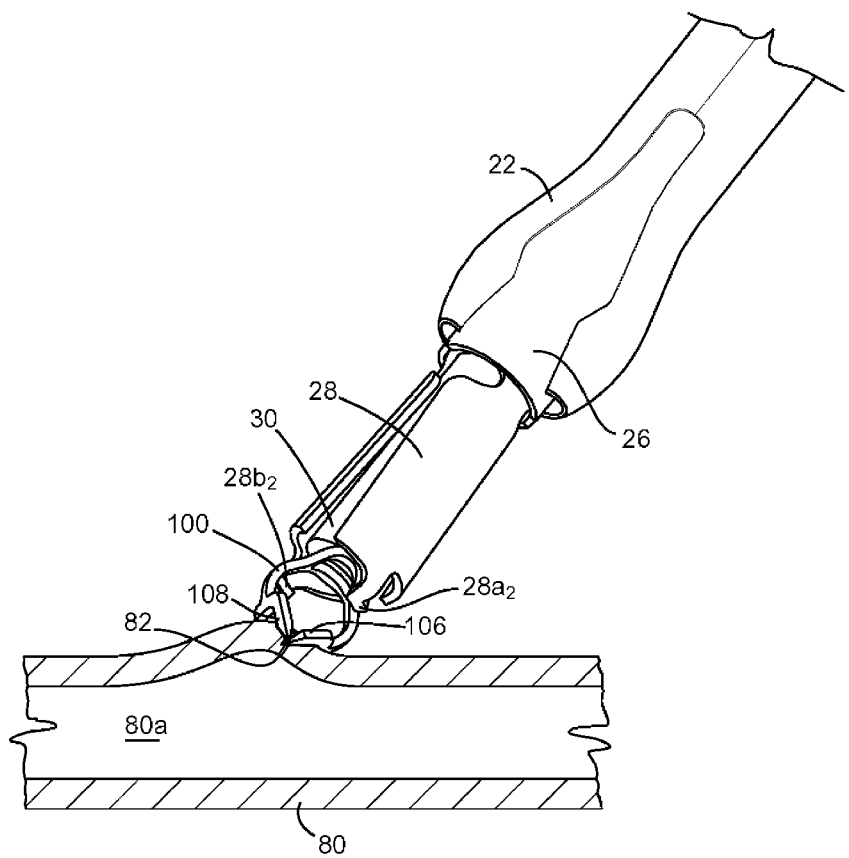
FIG. 25 is a side, partially cross-sectional perspective view of the staple applying apparatus shown in FIG. 22 showing the staple being released from the apparatus.
Figure 26:
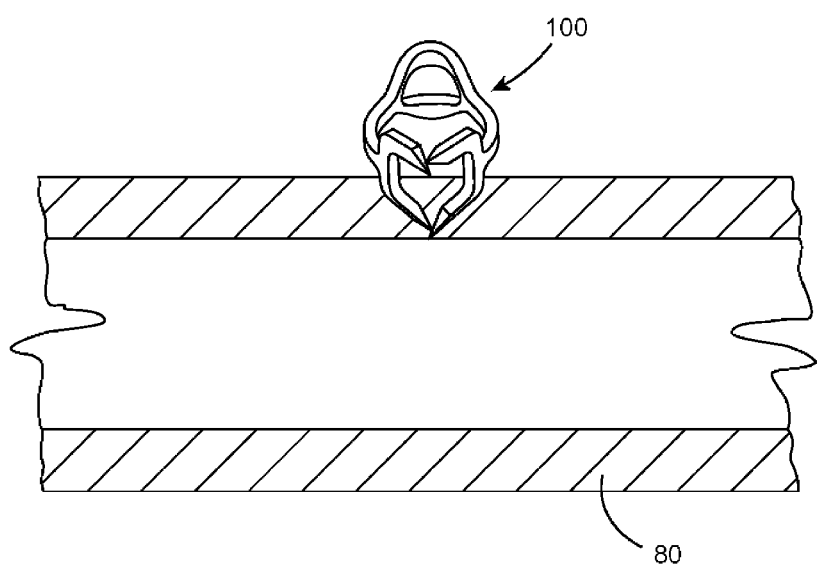
FIG. 26 is a side, partially cross-sectional perspective view of the locator tube and apparatus shown in FIG. 25 showing the staple positioned in the arterial wall.

Once closed, the former 26 and sheath 22 are both retracted to a position that allows the anvil arms 28 to spring outward thereby disengaging the anvil tangs 28a, 28b from the staple 100. A compression spring 37 (FIG. 12) pushing against the former bush 38b is used to drive the former 26 back causing the anvil arms 28 to spread open and disengage from the staple 100, as shown in FIGS. 25 and 26. Alternatively, the anvil 28 can be rotated 90 degrees so as to disengage the tangs 28a, 28b from the staple 100, and the former 26 and sheath 22 are retracted until the anvil arms 28 can deflect outward so that the staple 100 is free of the device 12. In both cases the pusher 30 may be used to apply a forward force to the staple 100 so that upon withdrawal of the anvil tangs 28a, 28b the staple 100 is advanced forward of the anvil 28. The device 12 may then be withdrawn from the tissue tract 84 and discarded. Prior to withdrawal of the device 12 from the tissue tract 84, the former 26 may be advanced over the anvil 28 causing the anvil arms to bend inward within the former 26 and thereby reducing the effective diameter of the deployment mechanism to be withdrawn through the subcuticular tissue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical stapler for closing a puncture wound in a liquid carrying vessel, comprising:
a locator tube having a proximal end and a distal end with an elongate lumen extending through at least a portion thereof for receiving a removable guide wire, the distal end being insertable into the liquid carrying vessel and the lumen extending from a guide wire entry port formed at the distal end of the locator tube toward a guide wire exit port formed in the locator tube and spaced proximally from the distal end of the locator tube, the guide wire exit port being distal to the proximal end of the locator tube, the locator tube further including a position indicator having a lumen extending through the locator tube and having a distal, blood inlet port formed in the locator tube and a proximal, blood outlet port formed in the locator tube, the locator tube further including an expandable member being formed radially about the locator tube and movable between a closed position and an open position, the expandable member distal end being proximal to the guide wire exit port and the guide wire entry port, the position indicator being effective to indicate a position of the expandable member relative to a liquid carrying vessel, the distal, blood inlet port in the locator tube being proximal and adjacent to the expandable member proximal end; and
a staple applying apparatus slidably disposed on a portion of the locator tube proximal to the expandable member and slidable over the blood outlet port, the staple applying apparatus being adapted to apply a surgical staple to seal a puncture wound in a liquid carrying vessel.

2. The surgical stapler of claim 1, wherein the locator tube has a locator tube longitudinal axis, the expandable member has an expandable member longitudinal axis, the elongate lumen for receiving the removable guide wire has a guide wire lumen longitudinal axis, and the position indicator lumen has a position indicator lumen longitudinal axis where the locator tube longitudinal axis, the expandable member longitudinal axis, the guide wire lumen longitudinal axis, and the position indicator lumen longitudinal axis are substantially collinear.

3. The surgical stapler of claim 1, wherein the expandable member comprises an inflatable balloon having a substantially constant diameter transverse to a longitudinal axis of the locator tube.

4. The surgical stapler of claim 1, wherein the staple applying apparatus includes a sheath having a staple pusher slidably disposed therein and adapted to push a staple against an anvil disposed within a distal end of the staple applying apparatus, and a staple former slidably disposed around the staple pusher and the anvil and adapted to deform a staple.

5. The surgical stapler of claim 4, wherein the sheath has a distal end that is expandable from a closed position, in which the sheath is adapted to be deployed through a tissue tract, and an open position, in which the sheath is retracted relative to the staple pusher, staple former, and anvil.

6. The surgical stapler of claim 5, wherein the distal end of the sheath includes opposed cut-out portions formed therein to allow the sheath to move between the open and closed positions.

7. The surgical stapler of claim 4, further comprising at least one staple having a central portion with an opening formed therein and disposed around the locator tube, and opposed legs extending distally from opposed ends of the central portion, the opposed legs being generally Y-shaped.

8. The surgical stapler of claim 7, wherein, when the staple is pushed against the anvil by the staple pusher, the anvil is adapted to move the legs a distance apart from one another such that the staple is adapted to be deployed into a liquid carrying vessel.

9. The surgical stapler of claim 7, wherein the at least one staple is bioabsorbable.

10. The surgical stapler of claim 9, wherein the at least one staple is formed from a magnesium alloy.

11. The surgical stapler of claim 1, wherein the expandable member is inflatable, and the locator tube includes an inflation lumen formed therein and coupled to a pressure relief valve that is adapted to regulate a pressure within the inflatable expandable member.

12. The surgical stapler of claim 1, wherein the blood inlet port is formed just proximal to the expandable member that the inlet port will be positioned external to a liquid carrying vessel when the expandable member is positioned against an internal surface of a liquid carrying vessel adjacent puncture wound.

13. A surgical stapler for closing a puncture wound in a liquid carrying vessel, comprising:
a locator tube having a proximal end and a distal end with an elongate lumen extending through at least a portion thereof for receiving a removable guide wire, the locator tube including a position indicator having a lumen extending through the locator tube and having a distal, blood inlet port formed in the locator tube and a proximal, blood outlet port formed in the locator tube, the locator tube further including an expandable member being formed radially about the locator tube and movable between a closed position and an open position, the position indicator being effective to indicate a position of the expandable member relative to a liquid carrying vessel, the distal, blood inlet port and the proximal, blood outlet port in the locator tube being proximal and adjacent to the expandable member proximal end prior to and at a time of stapling; and
a staple applying apparatus slidably disposed on a portion of the locator tube proximal to the expandable member and slidable over the blood outlet port, the staple applying apparatus being adapted to apply a surgical staple to seal a puncture wound in a liquid carrying vessel.

14. The surgical stapler of claim 13, wherein the locator tube has a locator tube longitudinal axis, the expandable member has an expandable member longitudinal axis, the elongate lumen for receiving the removable guide wire has a guide wire lumen longitudinal axis, and the position indicator lumen has a position indicator lumen longitudinal axis where the locator tube longitudinal axis, the expandable member longitudinal axis, the guide wire lumen longitudinal axis, and the position indicator lumen longitudinal axis are substantially collinear.

15. The surgical stapler of claim 13, wherein the expandable member comprises an inflatable balloon having a substantially constant diameter transverse to a longitudinal axis of the locator tube.

16. The surgical stapler of claim 13, wherein the staple applying apparatus includes a sheath having a staple pusher slidably disposed therein and adapted to push a staple against an anvil disposed within a distal end of the staple applying apparatus, and a staple former slidably disposed around the staple pusher and the anvil and adapted to deform a staple.

17. The surgical stapler of claim 16, wherein the sheath has a distal end that is expandable from a closed position, in which the sheath is adapted to be deployed through a tissue tract, and an open position, in which the sheath is retracted relative to the staple pusher, staple former, and anvil.

18. The surgical stapler of claim 17, wherein the distal end of the sheath includes opposed cut-out portions formed therein to allow the sheath to move between the open and closed positions.

19. The surgical stapler of claim 16, further comprising at least one staple having a central portion with an opening formed therein and disposed around the locator tube, and opposed legs extending distally from opposed ends of the central portion, the opposed legs being generally Y-shaped.

20. The surgical stapler of claim 19, wherein, when the staple is pushed against the anvil by the staple pusher, the anvil is adapted to move the legs a distance apart from one another such that the staple is adapted to be deployed into a liquid carrying vessel.

21. The surgical stapler of claim 19, wherein the at least one staple is bioabsorbable.

22. The surgical stapler of claim 21, wherein the at least one staple is formed from a magnesium alloy.

23. The surgical stapler of claim 13, wherein the expandable member is inflatable, and the locator tube includes an inflation lumen formed therein and coupled to a pressure relief valve that is adapted to regulate a pressure within the inflatable expandable member.

24. The surgical stapler of claim 13, wherein the blood inlet port is formed just proximal to the expandable member that the inlet port will be positioned external to a liquid carrying vessel when the expandable member is positioned against an internal surface of a liquid carrying vessel adjacent puncture wound.

25. A surgical stapler for closing a puncture wound in a liquid carrying vessel, comprising:
a locator tube including a position indicator that is effective to indicate a position of the expandable member relative to a liquid carrying vessel, the position indicator including an elongate lumen extending through the locator tube and having a distal, blood inlet port formed in the locator tube and a proximal, blood outlet port formed in the locator tube, the locator tube further including an expandable member formed radially about the locator tube and movable between a closed position and an open position, the distal, blood inlet port and the proximal, blood outlet port formed in the locator tube being proximal and adjacent to the expandable member proximal end prior to and at a time of stapling; and
a staple applying apparatus slidably disposed on a portion of the locator tube proximal to the expandable member and slidable over the blood outlet port, the staple applying apparatus being adapted to apply a surgical staple to seal a puncture wound in a liquid carrying vessel.

26. The surgical stapler of claim 25, wherein the locator tube has a locator tube longitudinal axis, the expandable member has an expandable member longitudinal axis, and the position indicator lumen has a position indicator lumen longitudinal axis where the locator tube longitudinal axis, the expandable member longitudinal axis, and the position indicator lumen longitudinal axis are substantially collinear.

27. The surgical stapler of claim 25, wherein the expandable member comprises an inflatable balloon having a substantially constant diameter transverse to a longitudinal axis of the locator tube.

28. The surgical stapler of claim 25, wherein the staple applying apparatus includes a sheath having a staple pusher slidably disposed therein and adapted to push a staple against an anvil disposed within a distal end of the staple applying apparatus, and a staple former slidably disposed around the staple pusher and the anvil and adapted to deform a staple.

29. The surgical stapler of claim 28, wherein the sheath has a distal end that is expandable from a closed position, in which the sheath is adapted to be deployed through a tissue tract, and an open position, in which the sheath is retracted relative to the staple pusher, staple former, and anvil.

30. The surgical stapler of claim 29, wherein the distal end of the sheath includes opposed cut-out portions formed therein to allow the sheath to move between the open and closed positions.

31. The surgical stapler of claim 28, further comprising at least one staple having a central portion with an opening formed therein and disposed around the locator tube, and opposed legs extending distally from opposed ends of the central portion, the opposed legs being generally Y-shaped.

32. The surgical stapler of claim 31, wherein, when the staple is pushed against the anvil by the staple pusher, the anvil is adapted to move the legs a distance apart from one another such that the staple is adapted to be deployed into a liquid carrying vessel.

33. The surgical stapler of claim 31, wherein the at least one staple is bioabsorbable.

34. The surgical stapler of claim 33, wherein the at least on staple is formed from a magnesium alloy.

35. The surgical stapler of claim 25, wherein the expandable member is inflatable, and the locator tube includes an inflation lumen formed therein and coupled to a pressure relief valve that is adapted to regulate a pressure within the inflatable expandable member.

36. The surgical stapler of claim 25, wherein the blood inlet port is formed just proximal to the expandable member that the inlet port will be positioned external to a liquid carrying vessel when the expandable member is positioned against an internal surface of a liquid carrying vessel adjacent puncture wound.

37. The surgical stapler of claim 25, wherein the locator tube includes a proximal end and a distal end with a lumen extending through at least a portion thereof for receiving a removable guide wire.

38. The surgical stapler of claim 37, wherein the distal end of the locator tube is insertable into the liquid carrying vessel and the lumen of the locator tube extends from a guide wire entry port at the distal end of the locator tube toward a guide wire exit port spaced proximally from the distal end of the locator tube, the guide wire exit port being distal to the proximal end of the locator tube.

39. A locator tube extending from a distal end toward a proximal end about a locator tube longitudinal axis, the locator tube comprising:

an elongate, flexible guide wire lumen extending through at least a portion of said locator tube having a guide wire lumen longitudinal axis, said guide wire lumen configured to receive a removable guide wire, said guide wire lumen extending from a guide wire entry port at said distal end of said locator tube toward a guide wire exit port spaced proximally from said distal end of said locator tube, said guide wire exit port being distal to said proximal end of said locator tube;

an expandable member having an expandable member proximal end, an expandable member distal end, and an expandable member longitudinal axis, said expandable member being formed radially about said locator tube and having a substantially constant diameter transverse to said locator tube longitudinal axis, said expandable member distal end being proximal to said guide wire exit port and said guide wire entry port;

a position indicator including a position indicator lumen extending through a portion of said locator tube and having a distal, blood inlet port, a proximal, blood outlet port, and a position indicator lumen longitudinal axis, said position indicator being configured to indicate a position of said expandable member relative to a liquid carrying vessel, said distal, blood inlet port being proximal and adjacent to said expandable member proximal end prior to and at said time of locating a body lumen such that said distal, blood inlet port will be external to an outer surface of the body lumen when said expandable member is positioned against an internal surface of the body lumen puncture wound; and an inflation lumen extending through said locator tube and having an inflation lumen longitudinal axis, said inflation lumen being configured to transition said expandable member between a closed position and an open position, said locator tube longitudinal axis being substantially collinear with at least one of said inflation lumen longitudinal axis and said position indicator lumen longitudinal axis.

\* \* \* \* \*